(12) United States Patent
Uemura et al.

(10) Patent No.: US 10,646,126 B2
(45) Date of Patent: May 12, 2020

(54) PORTABLE ELECTRONIC APPARATUS AND WRIST APPARATUS

(71) Applicant: SEIKO EPSON CORPORATION, Tokyo (JP)

(72) Inventors: Takehisa Uemura, Shiojiri (JP); Noriaki Hiraide, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 20 days.

(21) Appl. No.: 16/028,958

(22) Filed: Jul. 6, 2018

(65) Prior Publication Data
US 2019/0021617 A1 Jan. 24, 2019

(30) Foreign Application Priority Data

Jul. 19, 2017 (JP) .................. 2017-139733
Feb. 27, 2018 (JP) .................. 2018-032904

(51) Int. Cl.
| | |
|---|---|
| *H05K 5/00* | (2006.01) |
| *H05K 7/00* | (2006.01) |
| *A61B 5/024* | (2006.01) |
| *G06F 1/16* | (2006.01) |
| *A61B 5/00* | (2006.01) |
| *A61B 5/11* | (2006.01) |
| *G04G 21/02* | (2010.01) |
| *G06F 1/20* | (2006.01) |
| *H02S 20/30* | (2014.01) |
| *H01L 31/042* | (2014.01) |
| *G04C 10/04* | (2006.01) |

(Continued)

(52) U.S. Cl.
CPC ........ *A61B 5/02427* (2013.01); *A61B 5/1118* (2013.01); *A61B 5/1126* (2013.01); *A61B 5/681* (2013.01); *G04C 10/04* (2013.01); *G04G 21/025* (2013.01); *G04R 20/02* (2013.01); *G06F 1/163* (2013.01); *G06F 1/1635* (2013.01); *G06F 1/1684* (2013.01); *G06F 1/1694* (2013.01); *G06F 1/203* (2013.01); *H01L 31/042* (2013.01); *H02S 20/30* (2014.12); *A61B 5/0022* (2013.01); *A61B 5/01* (2013.01); *A61B 5/0402* (2013.01); *A61B 5/1112* (2013.01); *A61B 2560/0214* (2013.01); *A61B 2562/0219* (2013.01); *G04G 19/00* (2013.01); *H02S 99/00* (2013.01)

(58) Field of Classification Search
CPC ....................................................... H05K 5/00
See application file for complete search history.

(56) References Cited

U.S. PATENT DOCUMENTS

| | | |
|---|---|---|
| 2003/0181795 A1 | 9/2003 | Suzuki et al. |
| 2012/0120772 A1* | 5/2012 | Fujisawa ............... G04C 10/02 368/64 |
| 2014/0268522 A1* | 9/2014 | Tanaka ................... A61B 5/681 361/679.01 |

FOREIGN PATENT DOCUMENTS

JP 2006-320735 A 11/2006

* cited by examiner

*Primary Examiner* — Jerry Wu
(74) *Attorney, Agent, or Firm* — Oliff PLC

(57) ABSTRACT

A wrist apparatus as a portable electronic apparatus includes a case, a solar battery that is provided in the case, and has an outer circumference along an outer edge of the case and an inner circumference of which a circumferential length is shorter than a circumferential length of the outer circumference, and an acceleration sensor that is provided in the case, in which the solar battery is disposed outside an outer edge of the acceleration sensor in a plan view of a light reception surface of the solar battery.

4 Claims, 11 Drawing Sheets

(51) Int. Cl.
*G04R 20/02* (2013.01)
*H02S 99/00* (2014.01)
*G04G 19/00* (2006.01)
*A61B 5/0402* (2006.01)
*A61B 5/01* (2006.01)

PORTABLE ELECTRONIC APPARATUS AND WRIST APPARATUS

CROSS-REFERENCES TO RELATED APPLICATIONS

This application claims priority to Japanese Patents Application No. 2018-032904, filed Feb. 27, 2018, and No. 2017-139733, filed Jul. 19, 2017, all of which are herein incorporated by reference.

BACKGROUND

1. Technical Field

The present invention relates to a portable electronic apparatus and a wrist apparatus.

2. Related Art

In the related art, there is a portable electronic apparatus which is mounted on the wrist of a wearer with a band or the like, and has a function of measuring biological information such as a pulse wave of the wearer, or a clock display function. For example, JP-A-2006-320735 discloses a wearable life support apparatus which is mounted on the body of a wearer, and acquires biological information or body motion information by using a pulse wave sensor or acceleration sensor. In the wearable life support apparatus, since various sensors are operated to acquire biological information or body motion information for a long period of time (for example, a week), and thus power consumption increases, a method for reducing power consumption is proposed through power source management, for example, message display to a user is turned off during sleeping, or a specific sensor is stopped during sleeping.

However, in a case where various sensors including sensors with high power consumption, such as a GPS receiver or a pulse wave sensor, are mounted, not only power required to drive the sensors but also power required for a processor to process a large volume of data and power for wirelessly transmitting and receiving data are necessary, and thus it is hard to secure necessary power only through the power source management as in JP-A-2006-320735. In order not to impair the portability of a portable electronic apparatus, there is a restriction in increasing an apparatus size, and thus it is hard to simply increase a size of a secondary battery. Therefore, measures such as installing a power generation function such as a solar battery in a portable electronic apparatus are conceivable, but there is concern that a thickness of the portable electronic apparatus may increase due to mounting of the solar battery.

SUMMARY

An advantage of some aspects of the invention is to solve at least a part of the problems described above, and the invention can be implemented as the following forms or application examples.

APPLICATION EXAMPLE 1

A portable electronic apparatus according to this application example includes a case that has an opening which is open on one side; a solar battery that is provided in the case, and has an outer circumference located on an inner edge side of the opening and an inner circumference of which a circumferential length is shorter than a circumferential length of the outer circumference; and an acceleration sensor that is provided in the case, in which the solar battery is disposed outside an outer edge of the acceleration sensor in a plan view from a normal direction to a light reception surface of the solar battery.

According to the portable electronic apparatus according to this application example, the solar battery having the outer circumference located on the inner edge side of the opening and the inner circumference of which a circumferential length is shorter than a circumferential length of the outer circumference is disposed outside the outer edge of the acceleration sensor in the plan view from the normal direction to the light reception surface of the solar battery. In other words, the acceleration sensor can be disposed at a position not overlapping the solar battery inside the solar battery disposed along the outer edge of the case. Consequently, it is possible to realize thinning of the electronic apparatus more than in a case where the acceleration sensor overlaps the solar battery.

APPLICATION EXAMPLE 2

A portable electronic apparatus according to this application example includes a case; a display unit that is mounted on the case, and has a display surface on which information is displayed; a solar battery that is disposed outside the display surface in a plan view from a normal direction to the display surface; and an acceleration sensor that is mounted on the case, and is disposed at a position overlapping the display surface in the plan view.

According to the portable electronic apparatus according to this application example, the annular solar battery disposed outside the display surface is disposed outside the outer edge of the acceleration sensor in the plan view from the normal direction to the light reception surface of the solar battery. In other words, the acceleration sensor can be disposed at a position overlapping the display surface inside the solar battery disposed along the outer edge of the case. Consequently, it is possible to realize thinning of the electronic apparatus more than in a case where the acceleration sensor overlaps the solar battery.

APPLICATION EXAMPLE 3

It is preferable that the portable electronic apparatus according to the application example further includes a secondary battery that is provided in the case, and is electrically connected to the solar battery, and the secondary battery is preferably disposed at a position overlapping the acceleration sensor in the plan view.

According to this application example, since the secondary battery and the acceleration sensor are disposed at positions overlapping each other in the plan view, it is possible to increase a plane area of the secondary battery, that is, a power storage amount of the secondary battery can be increase more than in a case where the secondary battery does not overlap the acceleration sensor.

APPLICATION EXAMPLE 4

It is preferable that the portable electronic apparatus according to the application example further includes a processing unit that processes a signal from the acceleration sensor; and a resonator that is electrically connected to the processing unit, and the solar battery is preferably disposed outside an outer edge of the resonator in the plan view.

According to this application example, the solar battery is disposed outside the outer edge of the resonator in the plan view of the light reception surface of the solar battery. In other words, since the resonator and the solar battery are disposed at positions not overlapping each other, even if an area of the light reception surface of the solar battery is increased, it is possible to suppress the influence of radiant heat of the solar battery of which the temperature increases due to energy of light on the accuracy (a change in an oscillation frequency according to a temperature characteristic) of an oscillation frequency of the resonator.

APPLICATION EXAMPLE 5

It is preferable that the portable electronic apparatus according to the application example further includes a circuit board that is provided in the case, and is electrically connected to the acceleration sensor, and, in a sectional view from a direction orthogonal to the normal direction to the light reception surface, the secondary battery is disposed between the solar battery and the circuit board.

According to this application example, even if an area of the light reception surface of the solar battery is increased, radiant heat of the solar battery of which the temperature increases due to energy of light can be blocked by the secondary battery, and thus it is possible to reduce the influence of heat on detection in the acceleration sensor connected to the circuit board.

APPLICATION EXAMPLE 6

It is preferable that the portable electronic apparatus according to the application example further includes a biological information measurement unit that is provided in the case, and measures biological information, and the solar battery is disposed outside an outer edge of the biological information measurement unit in the plan view.

According to this application example, the solar battery is disposed outside the outer edge of the biological information measurement unit in the plan view. In other words, the biological information measurement unit is disposed on the center side of the case in the plan view, and thus the influence of external light on the biological information measurement unit can be reduced. Therefore, the solar battery can be disposed without lowering measurement accuracy in the biological information measurement unit.

Application Example 7

In the portable electronic apparatus according to the application example, it is preferable that, in the sectional view, the circuit board is disposed between the biological information measurement unit, and the solar battery.

According to this application example, it is possible to block so-called stray light which is light incident toward the solar battery for power generation but enters the inside of the case as leakage light through a gap or the like from the solar battery side, with the circuit board, and can thus to reduce the influence of external light on the biological information measurement unit.

APPLICATION EXAMPLE 8

In the portable electronic apparatus according to the application example, it is preferable that the circuit board has a first surface and a second surface which has a front-rear relationship with the first surface, and the solar battery and the acceleration sensor are connected to the first surface, and the biological information measurement unit is connected to the second surface.

According to this application example, routing of a wiring for connection can be made the minimum, and it is also possible to block stray light which is light incident for power generation but enters the inside of the case from the solar battery side, with the circuit board, and thus to reduce the influence of external light on the biological information measurement unit.

APPLICATION EXAMPLE 9

In the portable electronic apparatus according to the application example, it is preferable that the solar battery is disposed annularly in the plan view.

According to this application example, since the solar battery is disposed annularly, a display region can be efficiently disposed, and thus it is possible to increase designability of the portable electronic apparatus.

APPLICATION EXAMPLE 10

It is preferable that he portable electronic apparatus according to the application example further includes a circuit board that is provided in the case, the circuit board has a first surface and a second surface which has a front-rear relationship with the first surface, and the acceleration sensor and an illumination unit are provided on the first surface, and a biological information measurement unit measuring biological information is provided on the second surface.

According to this application example, routing of a wiring for connection can be made the minimum, and it is also possible to block light emitted from the illumination unit connected to the first surface with the circuit board, and can thus to reduce the influence of stray light on the biological information measurement unit connected to the second surface.

APPLICATION EXAMPLE 11

In the portable electronic apparatus according to the application example, it is preferable that the biological information measurement unit includes a light emitting portion and a light receiving portion, and the light emitting portion is disposed outside the light receiving portion in the plan view.

According to this application example, since the light receiving portion is located inside the light emitting portion, it is possible to suppress external light from entering the light receiving portion and thus to reduce the influence of the external light on the biological information measurement unit.

APPLICATION EXAMPLE 12

A wrist apparatus according to this application example includes a case; a display unit that is mounted on the case, and has a display surface on which information is displayed; a solar battery that is disposed outside the display surface in a plan view from a normal direction to the display surface; and an acceleration sensor that is mounted on the case, and is disposed at a position overlapping the display surface in the plan view.

According to the wrist apparatus according to this application example, the annular solar battery disposed outside the display surface is disposed outside the outer edge of the acceleration sensor in the plan view from the normal direction to the light reception surface of the solar battery. In other words, the acceleration sensor can be disposed at a position overlapping the display surface inside the solar battery disposed along the outer edge of the case. Consequently, it is possible to realize thinning of the wrist apparatus more than in a case where the acceleration sensor overlaps the solar battery.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
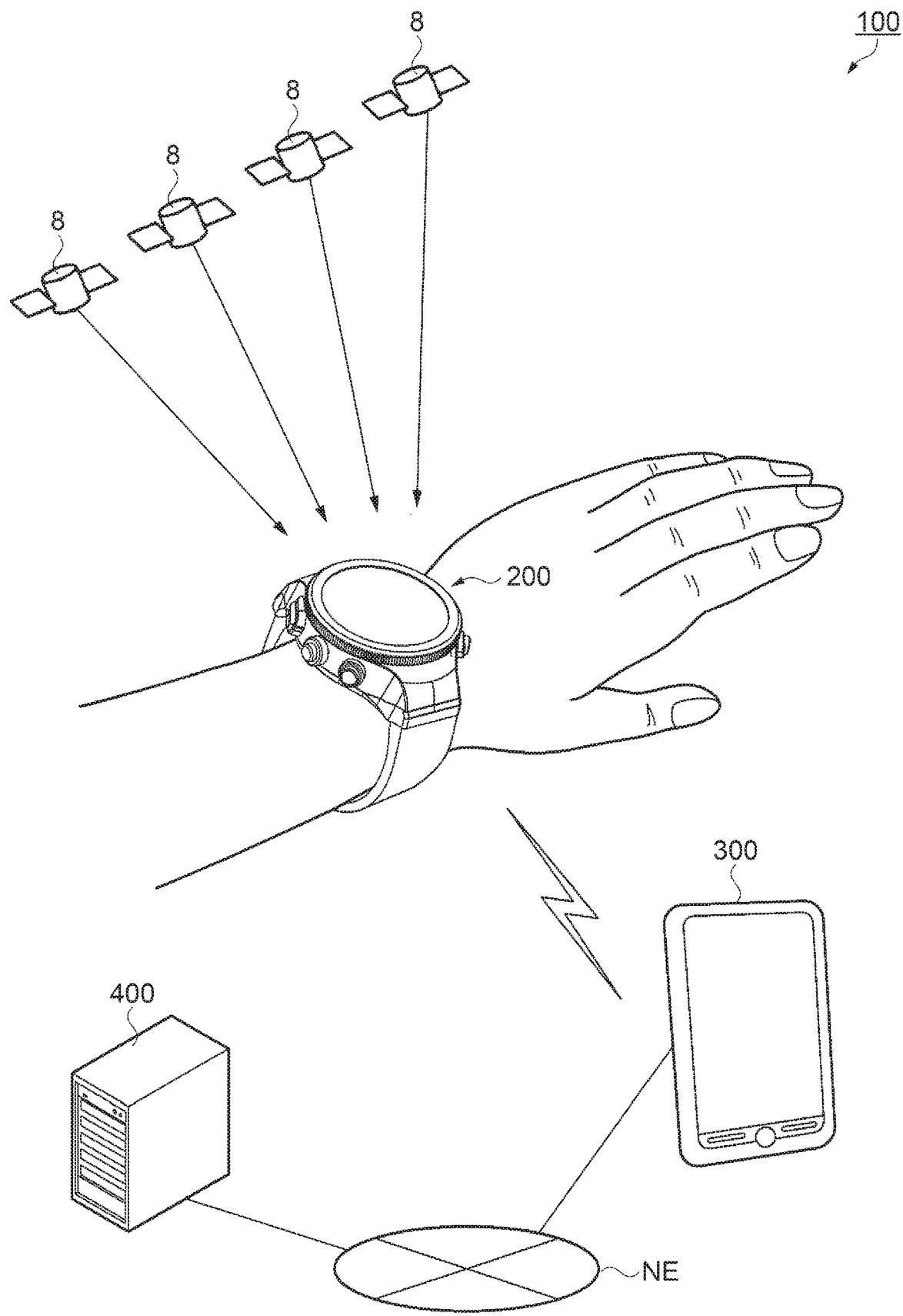
FIG. 1 is a schematic configuration diagram illustrating a summary of a workout support system to which a wrist apparatus as a portable electronic apparatus is applied.

Hereinafter, embodiments of a system related to the invention will be described. The embodiments described below are not intended to improperly limit the content of the invention disclosed in the appended claims. All constituent elements described in each embodiment are not essential constituent elements of the invention.

1. Method of Present Embodiment

First, a description will be made of a workout support system as an example of a system to which a portable electronic apparatus according to the present embodiment of the invention is applied. Hereinafter, as an example of a portable electronic apparatus, a description will be made of a wrist apparatus (wearable apparatus) which is mounted on the wrist of a user and includes a pulse wave sensor or a body motion sensor.

A wrist apparatus as a portable electronic apparatus used for a workout support system is provided with a solar battery on a display unit side, and includes a pulse wave sensor acquiring pulse wave information as biological information of a user or a body motion sensor acquiring action information of the user. The wrist apparatus includes a global positioning system (GPS) acquiring position information of the user as an example of a positioning system using a position information satellite called a global navigation satellite system (GNSS). A portable electronic apparatus is not limited to the wrist apparatus, and may be a wearable apparatus which is mounted on other parts of the user, such as the neck or the ankle.

The pulse wave sensor as an example of a biological information measurement unit acquires pulse wave information such as a pulse rate. As the pulse wave sensor, for example, a photoelectric sensor (optical sensor) is used. In this case, the photoelectric sensor may detect reflected light or transmitted light of light applied to a living body. Since an amount of applied light absorbed or reflected in the living body differs depending on a blood flow rate in a blood vessel, sensor information detected by the photoelectric sensor is converted into a signal corresponding to the blood flow rate, and information regarding pulsation can be acquired by analyzing the signal. However, a pulse wave sensor is not limited to a photoelectric sensor, and may employ other sensors such as an electrocardiograph or an ultrasonic sensor.

The photoelectric sensor (optical sensor) is required to receive necessary light and to block unnecessary light. For example, in a case of a pulse wave sensor, reflected light including a pulse wave component reflected at a subject (particularly, a part including a measurement target blood vessel) which is a measurement target object is required to be received, and other light is a noise component and is thus required to be blocked.

The body motion sensor is a sensor detecting motion of the user. As the body motion sensor, an acceleration sensor, an angular velocity sensor, an azimuth sensor (geomagnetic sensor), a pressure sensor (altitude sensor), or the like may be used, but other sensors may be used.

The GPS stands for a global positioning system, and is a satellite positioning system for measuring the current position on the earth on the basis of a plurality of satellite signals. The GPS has a function of acquiring position information of a user by performing positioning calculation by using GPS time information and orbit information, and a time correction function in a clock function.

2. Workout Support System

Next, with reference to FIG. 1, a description will be made of a configuration of a workout support system to which a wrist apparatus as a portable electronic apparatus is applied. FIG. 1 is a schematic configuration diagram illustrating a summary of a workout support system to which a wrist apparatus as a portable electronic apparatus is applied.

A workout support system 100 according to the present embodiment includes, as illustrated in FIG. 1, a wrist apparatus 200 as a portable electronic apparatus which is a detection apparatus including a pulse wave sensor as a biological sensor (photoelectric sensor), an acceleration sensor as a body motion sensor, and a GPS; a portable apparatus 300 as a workout support apparatus; and a server 400 as an information processing apparatus which is connected to the portable apparatus 300 via a network NE.

The GPS as a global navigation satellite system provided in the wrist apparatus 200 has a function of receiving electric waves (satellite signals) from GPS satellites 8, and correcting internal time or acquiring position information by positioning calculation. Each of the GPS satellites 8 is an example of a position information satellite which orbits on a predetermined orbit in the sky above the earth and transmits high-frequency electric waves superimposed with a navigation message to the ground. In the following description, an electric wave superimposed with a navigation message will be referred to as a satellite signal.

A satellite signal from the GPS satellite 8 includes GPS time information which is considerably accurate, and a time correction parameter for correcting a time error. The wrist apparatus 200 may receive a satellite signal (electric wave) from a single GPS satellite 8 so as to acquire time information by using the GPS time information and the time correction parameter included therein.

The satellite signal also includes orbit information indicating a position on an orbit of the GPS satellite 8. The wrist apparatus 200 may perform positioning calculation by using the GPS time information and the orbit information. The positioning calculation is performed on the premise that some extent of an error is included in an internal time of the wrist apparatus 200. In other words, a time error is also an unknown number in addition to x, y and z parameters for specifying a three-dimensional position of the wrist apparatus 200. Thus, the wrist apparatus 200 may receive satellite signals (electric waves) transmitted from, for example, three or more GPS satellites 8, and may perform positioning calculation by using GPS time information and orbit information included therein so as to acquire position information of the current location.

The portable apparatus 300 as a workout support apparatus may be formed of, for example, a smart phone or a tablet terminal apparatus. The portable apparatus 300 is connected to the wrist apparatus 200 in which a pulse wave sensor as a biological sensor which is a photoelectric sensor and an acceleration sensor as a body motion sensor are used via short-range radio communication such as Bluetooth (registered trademark) communication or wired communication (not illustrated). The portable apparatus 300 receives measurement information from the wrist apparatus 200, and notifies a user of processed pulse wave information or body motion information of the user, or position information. However, the portable apparatus 300 may be variously modified, for example, by including an optical sensor unit 40, a body motion sensor unit 170, or a GPS reception unit 160 which will be described later included in the wrist apparatus 200.

The wrist apparatus 200 and the portable apparatus 300 have a Bluetooth function, and the portable apparatus 300 and the wrist apparatus 200 are connected to each other via Bluetooth communication, for example, Bluetooth Low Energy (also called Bluetooth 4.0). Bluetooth Low Energy focuses on power saving, and can considerably save power compared with an old version so as to increase available time of the wrist apparatus.

The portable apparatus 300 may be connected to the server 400 such as a personal computer (PC) or a server system via the network NE. The network NE here may employ various networks NE such as a wide area network (WAN), a local area network (LAN), a mobile phone communication network, and short-range radio communication. In this case, the server 400 is realized as a processing storage unit which receives pulse wave information or body motion information measured by the wrist apparatus 200 or data processed by the portable apparatus 300 from the portable apparatus 300 via the network NE, and stores the information or the data.

In the embodiment, the wrist apparatus 200 is not required to be directly connected to the network NE as long as the wrist apparatus 200 can perform communication with the portable apparatus 300. Therefore, a configuration of the wrist apparatus 200 can be simplified. However, in the workout support system 100, a modification may occur in which the portable apparatus 300 is omitted, and the wrist apparatus 200 is directly connected to the server 400. In this case, the wrist apparatus 200 has a function, which is a function of the portable apparatus 300, of processing measurement information, and a function of transmitting measurement information to the server 400 or receiving information from the server 400.

The workout support system 100 is not limited to a configuration including the server 400. For example, processes or functions performed in the workout support system 100 may be realized by the portable apparatus 300. For example, the portable apparatus 300 such as a smart phone has restrictions in processing capability, a storage region, and a battery capacity compared with a server system, but may secure sufficient processing capability and the like in consideration of the recent capability improvement. Therefore, if the needs for the processing capability and the like are satisfied, the portable apparatus 300 can independently realize processes or functions performed in the workout support system 100 according to the present embodiment.

The workout support system 100 according to the present embodiment is not limited to being realized by three apparatuses. For example, the workout support system 100 may include two or more apparatuses among the wrist apparatus 200, the portable apparatus 300, and the server 400. In this case, processes performed in the workout support system 100 may be performed by any one of apparatuses, and may be distributed to and performed by a plurality of apparatuses. The workout support system 100 according to the present embodiment may include apparatuses which are different from the wrist apparatus 200, the portable apparatus 300, and the server 400. However, in a case of taking into consideration improvement of terminal capability or a use form, there may be an embodiment in which the workout support system 100 according to the present embodiment is realized by the wrist apparatus 200.

The workout support system 100 of the present embodiment includes a memory storing information (for example, programs or pieces of data), and a processor which operates on the basis of the information stored in the memory. In the processor, for example, a function of each unit may be realized by individual hardware, and may be realized by integrated hardware. The processor may be, for example, a central processing unit (CPU). However, the processor is not limited to a CPU, and may employ various processors such as a graphics processing unit (GPU) or a digital signal processor (DSP). The processor may be a hardware circuit using an ASIC. The memory may be, for example, a semiconductor memory such as a static random access memory (SRAM) or a dynamic random access memory (DRAM), may be a register, may be a magnetic storage device such as a hard disk device, and may be an optical storage device such as an optical disc device. For example, the memory stores computer readable commands, and the commands are executed by the processor such that a function of each unit of the workout support system 100 is realized. The commands here may be commands forming a program, and may be commands for instructing a hardware circuit to perform an operation.

3. Wrist Apparatus

Figure 2:
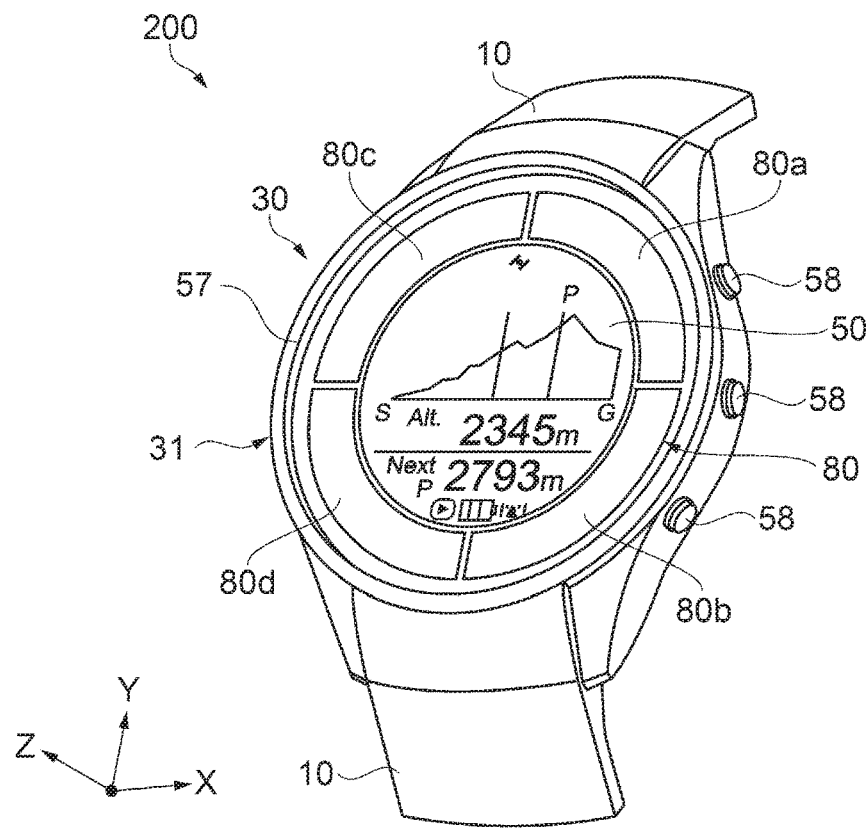
FIG. 2 is an exterior perspective view from a front side (display surface side) illustrating a schematic configuration of the wrist apparatus.
Figure 3:
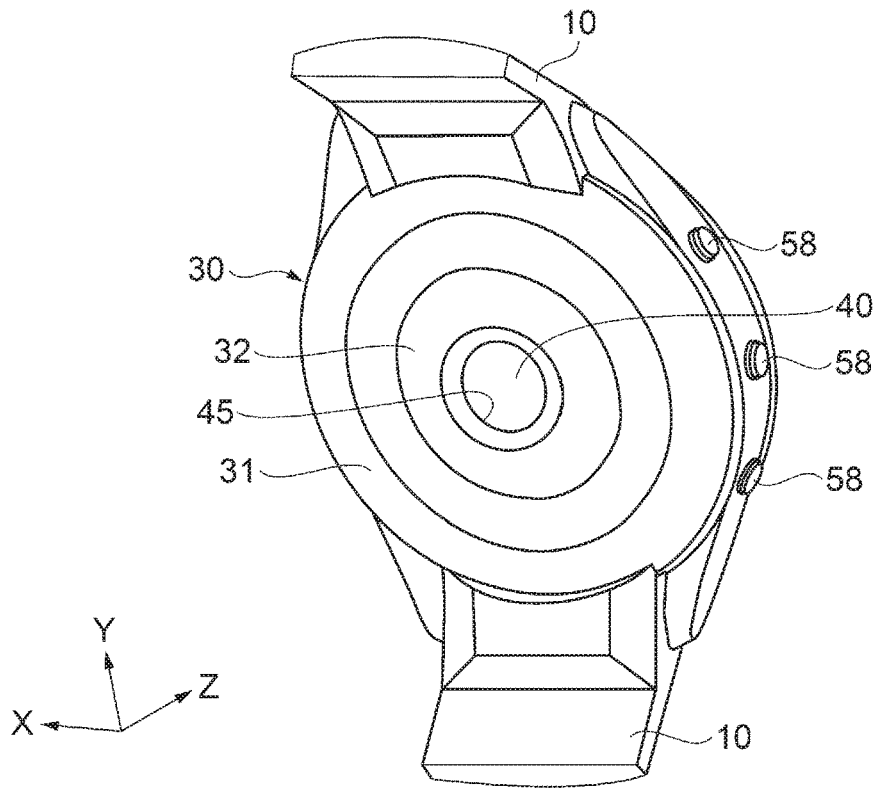
FIG. 3 is an exterior perspective view from a rear side illustrating a schematic configuration of the wrist apparatus.
Figure 4:
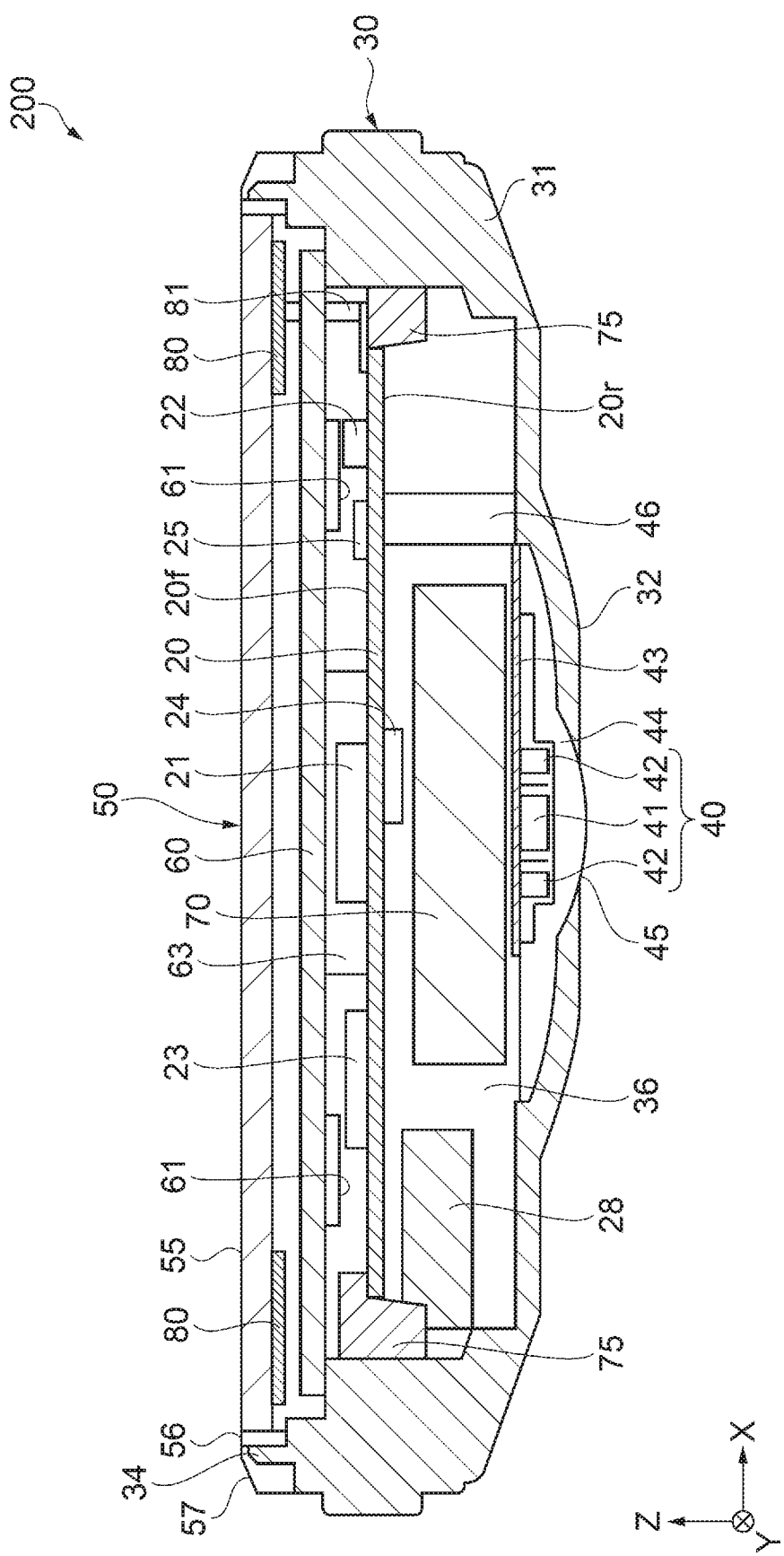
FIG. 4 is a sectional view illustrating a configuration of the wrist apparatus.
Figure 5A:
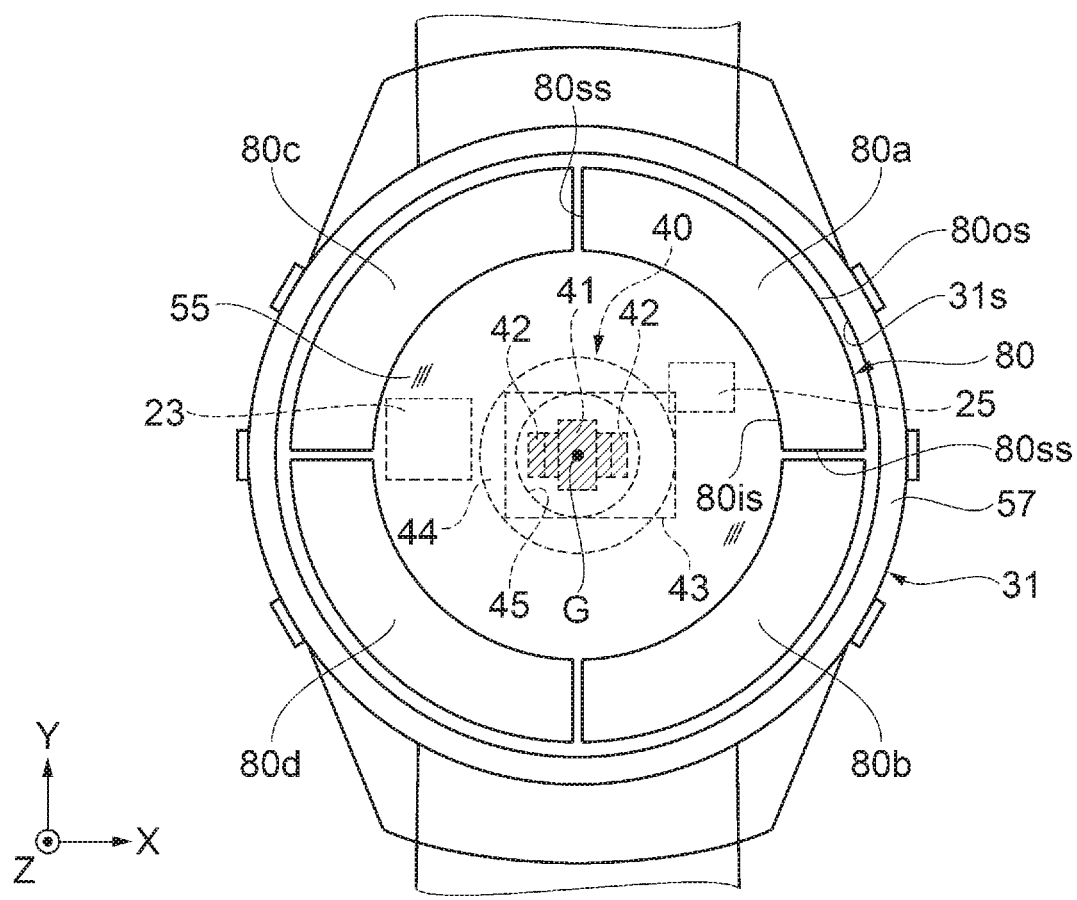
FIG. 5A is a plan view illustrating a configuration of the wrist apparatus.
Figure 6:
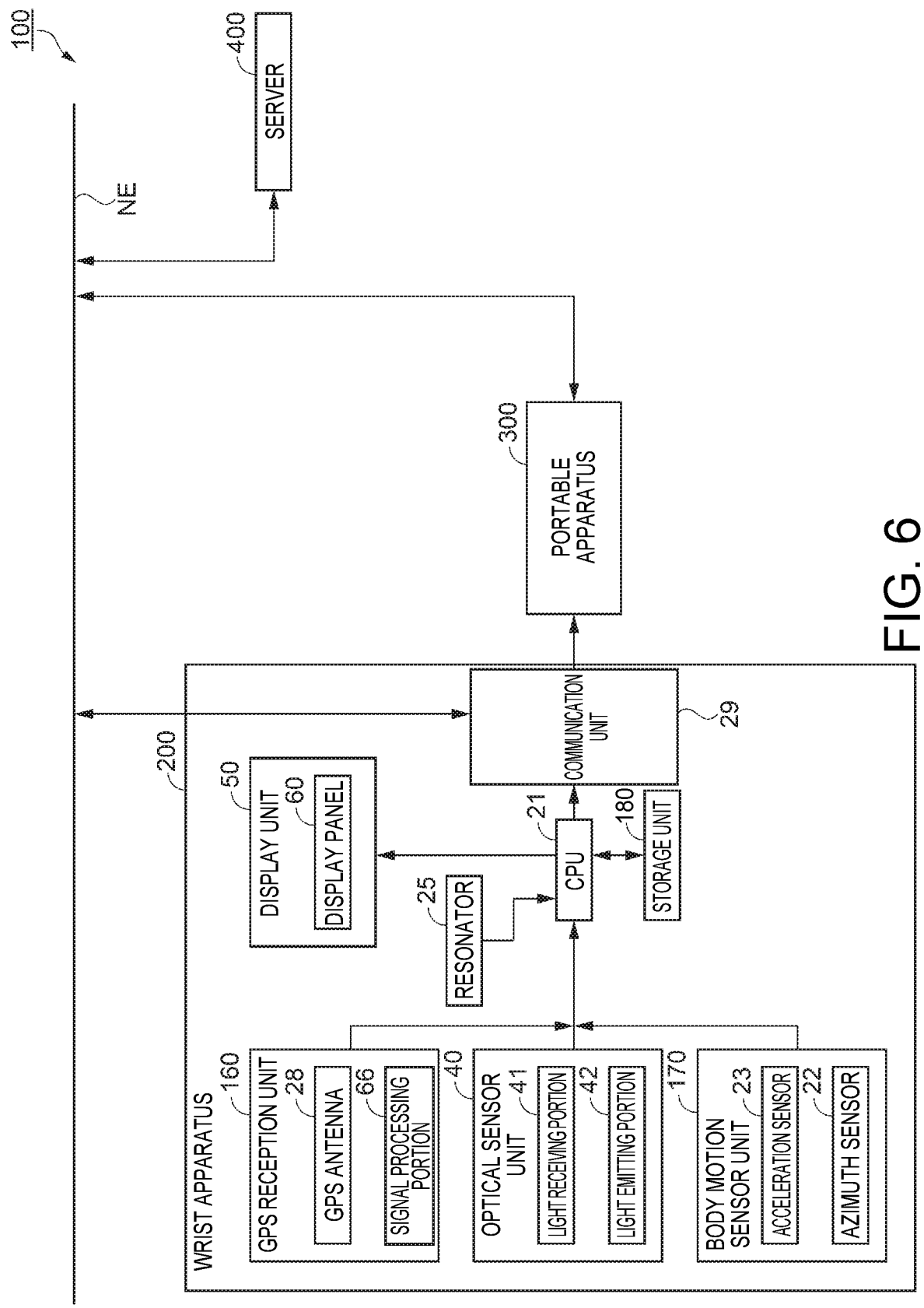
FIG. 6 is a functional block diagram illustrating a schematic configuration of the wrist apparatus.
Figure 7:
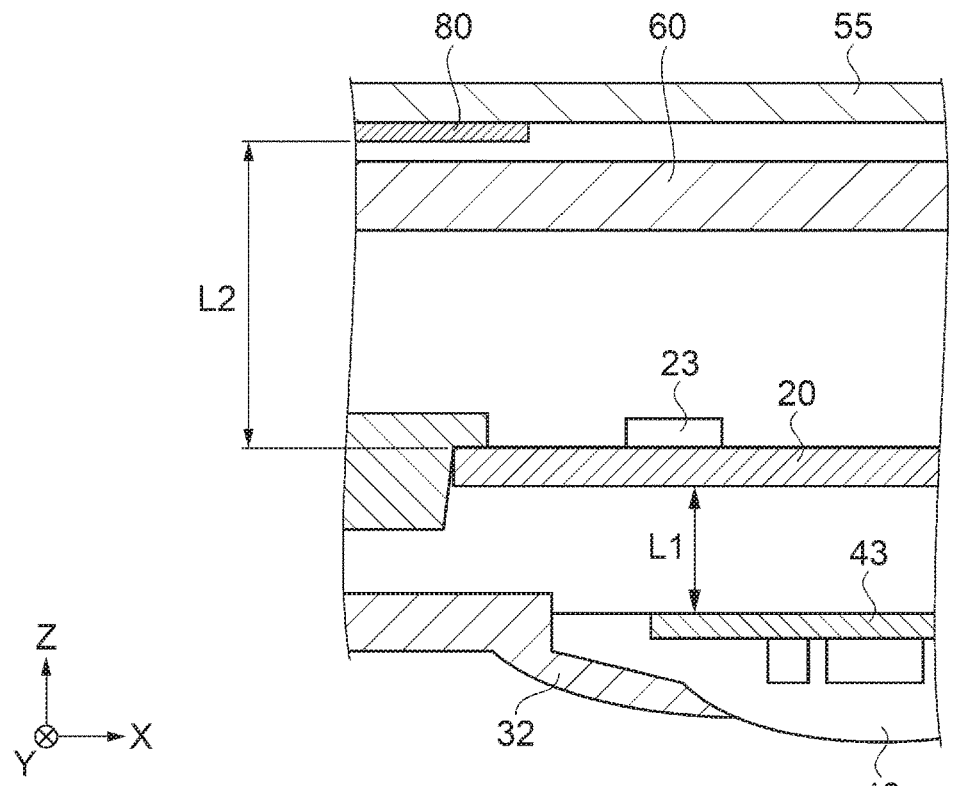
FIG. 7 is a partial sectional view illustrating a disposition example 1 of constituent elements of the wrist apparatus.
Figure 8:
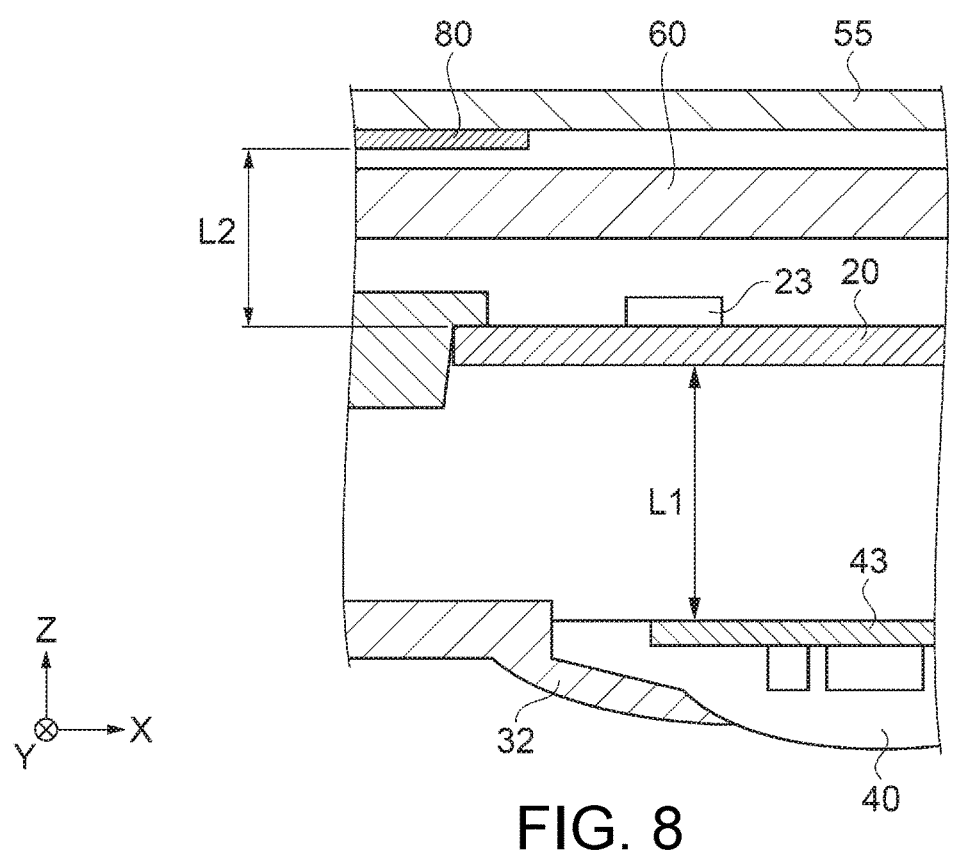
FIG. 8 is a partial sectional view illustrating a disposition example 2 of constituent elements of the wrist apparatus.

Next, with reference to FIGS. 2, 3, 4, 5A, 6, 7, and 8, a description will be made of a configuration of the wrist apparatus (measurement apparatus) as a portable electronic apparatus. FIG. 2 is an exterior perspective view from a front side (display surface side) illustrating a schematic configuration of the wrist apparatus. FIG. 3 is an exterior perspective view from a rear side illustrating a schematic configuration of the wrist apparatus. FIG. 4 is a sectional view illustrating a configuration of the wrist apparatus. FIG. 5A is a plan view illustrating a configuration of the wrist apparatus. FIG. 6 is a functional block diagram illustrating a schematic configuration of the wrist apparatus. FIG. 7 is a partial sectional view illustrating a disposition example 1 of constituent elements of the wrist apparatus. FIG. 8 is a partial sectional view illustrating a disposition example 2 of constituent elements of the wrist apparatus.

In the following description of the wrist apparatus 200, when an apparatus main body 30 is worn by a user, a side located on a target object side which is a target part for measuring biological information or the like will be referred to as "a rear side or a rear surface side", and a display surface side of the apparatus main body 30 opposite side thereto will be referred to as "a front side or a front surface side". A measurement "target object (target part)" will be referred to as a "subject" in some cases. A coordinate system is set with a case 31 of the wrist apparatus 200 as a reference, the center of a display surface of the display unit 50 is set to the origin, and a direction which is orthogonal to the display surface of the display unit 50, and is directed from a rear surface toward a front surface corresponding to the display surface side of the display unit 50 is defined as a positive Z axis direction (+Z axis direction). Alternatively, a direction which is directed from the optical sensor unit 40 toward the display unit 50 or becomes distant from the case 31 in a normal direction to light reception surfaces 80a, 80b, 80c, and 80d of a panel forming a solar battery 80 is defined as a positive Z axis direction. In a state in which the wrist apparatus 200 is worn on a subject, the positive Z axis direction corresponds to a direction directed from the subject toward the case 31. Two axes orthogonal to the Z axis are defined as XY axes, and, particularly, a direction in which band portions 10 are attached to the case 31 is set to the Y axis. The light reception surfaces 80a, 80b, 80c, and 80d are surfaces via which light is incident to the solar battery 80. In the present specification, the display unit 50 collectively indicates a region in which information which can be visually recognized through the windshield plate 55 from the +Z axis direction is displayed on a liquid crystal display (display panel 60). The display surface of the display unit 50 indicates a surface located on the front surface (a side on which the windshield plate 55 is disposed) of the liquid crystal display (display panel 60).

FIG. 2 is a perspective view in which the wrist apparatus 200 to which the band portion 10 is fixed is viewed from the +Z axis direction which is a direction directed toward the front side (display unit 50 side) which is opposite to the rear side corresponding to a subject side in a mounting state. FIG. 3 is a perspective view in which the wrist apparatus 200 is viewed from the rear side opposite to FIG. 2, that is, from the −Z axis direction. FIG. 4 is a sectional view in which the wrist apparatus 200 is viewed from the +Y axis direction. FIG. 5A is a plan view in which the wrist apparatus 200 is viewed from the +Z axis direction.

As illustrated in FIGS. 2 to 4, the wrist apparatus 200 as a portable electronic apparatus is mounted on a predetermined part (for example, a measurement target part such as the wrist) of the user, and measures pulse wave information, body motion information, position information, or the like. The wrist apparatus 200 includes the apparatus main body 30 which includes the case 31 and is in close contact with the user so as to measure pulse wave information, body motion information or the like, and a pair of band portions 10 which is attached to the apparatus main body 30 and is used to mount the apparatus main body 30 on the user.

The apparatus main body 30 including the case 31 is provided with the display unit 50, the annular solar battery 80 including the light reception surfaces 80a, 80b, 80c, and 80d of the panel disposed at an outer edge part of the display unit 50 and directed in the Z axis direction, and a measurement window portion 45 corresponding to the optical sensor unit 40 (refer to FIG. 4) as a biological information measurement unit. The display unit 50 and a part of the solar battery 80 may be disposed to overlap each other in a plan view from the +Z axis direction (the normal direction to the light reception surfaces 80a, 80b, 80c, and 80d). However, the solar battery 80 is disposed so as not to overlap a region (display surface) in which information is displayed on the liquid crystal display (display panel 60). A plurality of operation units (operation buttons) 58 are provided on an outer surface of the apparatus main body 30, and a bezel 57 is provided to annularly surround an outer edge of the display unit 50. However, the wrist apparatus 200 is not limited to such a configuration, and may be variously modified by omitting some of the constituent elements or adding other constituent elements thereto.

The apparatus main body 30 has the case 31 provided with an opening 31s which is open on the front side. The measurement window portion 45 of the optical sensor unit 40 is provided at the top of a protrusion portion 32 protruding from the rear surface which is a rear side surface of the case 31 on the rear side of the case 31. The optical sensor unit 40 as a biological information measurement unit is disposed at a position corresponding to the measurement window portion 45 in a plan view from the +Z axis direction, and the transparent cover 44 is inserted into the measurement window portion 45. The transparent cover 44 may protrude from the top of the protrusion portion 32. In a plan view from the +Z axis direction, the measurement window portion 45 is preferably disposed at a position not overlapping the solar battery 80. As mentioned above, since the measurement window portion 45 of the optical sensor unit 40 is disposed at the position not overlapping the solar battery 80, and thus a distance from the outer edge of the case 31 to the optical sensor unit 40 increases, external light hardly reaches the measurement window portion 45 such that external light can be suppressed from entering the measurement window portion 45, so that it is possible to prevent a reduction in measurement accuracy of biological information in the optical sensor unit 40.

The case 31 may be formed by using, for example, metal such as stainless steel, or a resin. A configuration of the case 31 is not limited to an integrated configuration, and may be a configuration of being divided into a plurality of parts, for example, the case 31 may have a dual structure in which a lid is provided on the side mounted on a user.

The apparatus main body 30 is provided with the bezel 57 on an outer circumferential side of a projection 34 which projects and stands in the +Z axis direction at the outer edge of the opening 31s of the case 31 located on the front side of the apparatus main body 30, and is also provided with a windshield plate 55 (a glass plate in this example) which is a transparent plate as a top plate for protecting the internal structure inside the bezel 57. The windshield plate 55 is disposed to close the opening of the case 31 in a plan view from a direction facing the light reception surfaces 80a, 80b, 80c, and 80d of the solar battery 80, that is, from the +Z axis direction. The windshield plate 55 is attached on an inner edge side of the projection 34 of the case 31 via a joint member 56 such as a packing or an adhesive. An internal space 36 which is a closed space is provided inside the case 31 surrounded by the case 31 and the windshield plate 55 closing the opening of the case 31.

The windshield plate 55 is not limited to a glass plate, and may be a member which is a light-transmissive member through which the display unit 50 can be viewed and is made of materials such as transparent plastic other than glass as long as the materials have the strength sufficient to protect element components accommodated in the internal space 36, for example, a liquid crystal display (display panel 60) forming the display unit 50.

As illustrated in FIG. 4, as element components forming the wrist apparatus 200, for example, a circuit board 20, an azimuth sensor 22 and an acceleration sensor 23 as sensors included in the body motion sensor unit 170 (refer to FIG. 6), a resonator 25 as a timing device which outputs a clock signal, a GPS antenna 28, the optical sensor unit 40, the liquid crystal display (hereinafter, referred to as the display panel 60) forming the display unit 50, an illumination unit 61 of the display panel 60, a secondary battery 70 (lithium secondary battery), and the solar battery 80 are stored in the internal space 36 of the case 31. However, the apparatus main body 30 is not limited to the configuration illustrated in FIG. 4, and may be added with other sensors such as a pressure sensor for calculating an elevation or a temperature sensor for measuring a temperature, or a vibrator. The circuit board 20 is connected to connection wires with the above-described element components, a central processing unit (CPU) 21 which is a control circuit controlling the respective sensors forming the wrist apparatus 200 or the display unit 50 or a control circuit including a drive circuit, the resonator 25, and other circuit elements 24. The CPU 21 as a processing unit may process signals detected by various sensors, for example, the optical sensor unit 40 or the acceleration sensor 23. The circuit board 20 may be connected to the azimuth sensor 22 or the acceleration sensor 23.

Among the element components forming the wrist apparatus 200 disposed in the internal space 36, the circuit board 20, the optical sensor unit 40, the secondary battery 70, the display panel 60, and the solar battery 80 are disposed in an order of the solar battery 80, the display panel 60, the circuit board 20, the secondary battery 70, and the optical sensor unit 40 from the windshield plate 55 side in the −Z axis direction. The solar battery 80 is disposed to cover at least a part of the display unit 50.

As mentioned above, the display panel 60 forming the display unit 50 is disposed between the solar battery 80 and the circuit board 20 in the case 31, and thus the user can easily visually recognize display on the display unit 50 without being blocked by the circuit board 20.

As mentioned above, since the display panel 60 forming the display unit 50 is disposed between the solar battery 80 and the optical sensor unit 40 in the case 31, it is possible to block so-called stray light which is light incident toward the solar battery 80 for power generation but enters the inside of the case 31 as leakage light through a gap or the like from the solar battery 80 side, with the display panel 60, and thus to reduce the influence of external light (stray light) on the optical sensor unit 40.

The secondary battery 70 is disposed between the display unit 50 and the optical sensor unit 40 in the case 31, and thus it is possible to block stray light which is light incident for power generation but enters the inside of the case 31 from the solar battery 80 side, with the secondary battery 70, and thus to reduce the influence of external light on the optical sensor unit 40.

As illustrated in FIG. 7, preferably, the circuit board 20, the optical sensor unit 40, and the solar battery 80 are disposed such that a distance L2 (the shortest distance between the circuit board 20 and the solar battery 80) between the circuit board 20 and the solar battery 80 is longer than a distance L1 (the shortest distance between the circuit board 20 and the optical sensor unit 40) between the circuit board 20 and the optical sensor unit 40 in a sectional view from the −Y axis direction which is orthogonal to the +Z axis direction (the normal direction to the light reception surfaces 80a, 80b, 80c, and 80d). As mentioned above, if the distance L2 between the circuit board 20 and the solar battery 80 is made long, the solar battery 80 is hardly influenced by heat generation from the circuit board 20 or other constituent elements. In other words, it is possible to suppress a temperature increase in the solar battery 80 and thus to suppress a reduction in power generation efficiency in the solar battery 80.

As illustrated in FIG. 8, the circuit board 20, the optical sensor unit 40, and the solar battery 80 are disposed such that the distance L2 (the shortest distance between the circuit board 20 and the solar battery 80) between the circuit board 20 and the solar battery 80 may be shorter than the distance L1 (the shortest distance between the circuit board 20 and the optical sensor unit 40) between the circuit board 20 and the optical sensor unit 40 in a sectional view from the −Y axis direction which is orthogonal to the +Z axis direction (the normal direction to the light reception surfaces 80a, 80b, 80c, and 80d). As mentioned above, if the distance L2 between the circuit board 20 and the solar battery 80 is made short, a transmission loss of power generated by the solar battery 80 can be reduced, and thus it is possible to increase charging efficiency.

Since the circuit board 20 is disposed between the solar battery 80 and the optical sensor unit 40 in the case 31, it is possible to block so-called stray light which is light incident toward the solar battery 80 for power generation but enters the inside of the case 31 as leakage light through a gap or the like from the solar battery 80 side, with the circuit board 20, and thus to reduce the influence of external light (stray light) on the optical sensor unit 40.

Hereinafter, each element component will be described also with reference to the functional block diagram of FIG. 6.

The circuit board 20 has a front surface 20f as a first surface and a rear surface 20r as a second surface which is different from the front surface 20f and is an opposite surface to the front surface 20f, and ends thereof are attached to a circuit case 75 which is a circuit fixing portion so as to be supported inside the case 31 via the circuit case 75. The azimuth sensor 22 and the acceleration sensor 23 as sensors included in the body motion sensor unit 170, the resonator 25 as a timing device, the CPU 21 as a control circuit, and the like are mounted on and electrically connected to the front surface 20f of the circuit board 20. Other circuit elements 24 and the like are mounted on and electrically connected to the rear surface 20r of the circuit board 20.

The display panel 60 and the solar battery 80 are connected to the front surface 20f of the circuit board 20 via a connection wiring portion 63 and a connection wiring portion 81 formed of flexible boards or the like. The optical sensor unit 40 is electrically connected to the rear surface 20r of the circuit board 20 which is an opposite surface to the front surface 20f via a connection wiring portion 46 formed of a flexible board or the like. With such disposition, routing of a wiring for connection can be made the minimum, and it is also possible to block stray light which is light incident for power generation but enters the inside of the case as leakage light from the solar battery 80 side, with the circuit board 20, and thus to reduce the influence of external light on the optical sensor unit 40. The circuit case 75 can guide the secondary battery 70 or the like.

The azimuth sensor (geomagnetic sensor) 22 or the acceleration sensor 23 included in the body motion sensor unit 170 may measure information related to motion of the user's body, that is, body motion information. The azimuth sensor (geomagnetic sensor) 22 or the acceleration sensor 23 outputs a body motion detection signal which is a signal changing depending on movement or turning of the user, and transmits the body motion detection signal to the CPU 21 as a processing unit including a control circuit. In addition to detection related to an action such as movement of the user, for example, the acceleration sensor 23 may perform detection based on a so-called tapping action of indicating the user's intention by applying light impact to the case 31 by tapping the outer circumferential portion of the case 31 or the windshield plate 55 with the fingertip.

As illustrated in FIG. 5A, the acceleration sensor 23 is preferably disposed such that the solar battery 80 is located outside the outer edge of the acceleration sensor 23 in a plan view from the +Z axis direction. In other words, the acceleration sensor 23 is preferably disposed not to overlap the solar battery 80 in a plan view from the +Z axis direction.

As mentioned above, since the solar battery 80 is disposed outside the outer edge of the acceleration sensor 23 in a plan view from the +Z axis direction, that is, the acceleration sensor 23 and the solar battery 80 are disposed at positions not overlapping each other, the apparatus main body 30 can be thinned more than in a case where the acceleration sensor 23 and the solar battery 80 overlap each other. Since the acceleration sensor 23 and the solar battery 80 are disposed at the positions not overlapping each other, even if areas of the light reception surfaces 80a, 80b, 80c, and 80d of the solar battery 80 are increased, it is possible to suppress the influence on detection accuracy in the acceleration sensor 23 due to radiant heat of the solar battery 80 of which the temperature increases due to energy of light. Therefore, it is possible to increase a power generation amount of the solar battery 80.

The acceleration sensor 23 is preferably disposed at a position overlapping the secondary battery 70 in a plan view from the +Z axis direction. As mentioned above, since the acceleration sensor 23 and the secondary battery 70 can be disposed at the positions overlapping each other in a plan view from the +Z axis direction, a plane area of the secondary battery 70 can be increased more than in a case where the secondary battery 70 and the acceleration sensor 23 are disposed at positions not overlapping each other, and thus it is possible to increase a power storage amount of the secondary battery 70.

The CPU 21 as a processing unit forms a control circuit or the like controlling a circuit which controls the GPS reception unit 160 including the GPS antenna 28, a circuit which drives the optical sensor unit 40 so as to measure a pulse wave, a circuit which drives the display unit 50 (display panel 60), a circuit which drives the body motion sensor unit 170 and processes a detected signal so as to measure body motion information, and a power generation circuit in the solar battery 80. The CPU 21 transmits pulse wave information or body motion information measured at each part, or position information of the user to a communication unit 29 as necessary.

The resonator 25 as a timing device outputting a reference signal generates reference clock signals such as a reference signal for a clock function or timing reference signals for various data processes, and outputs the reference clock signals to the CPU 21. The resonator 25 is configured to be accommodated in a ceramic package or the like into which a resonance element made of a piezoelectric material such as quartz crystal is built. FIG. 4 illustrates a single resonator 25, but a plurality of resonators 25 having output frequencies may be used.

As illustrated in FIG. 5A, the resonator 25 is preferably disposed such that the solar battery 80 is located outside the outer edge of the resonator 25 in a plan view from the +Z axis direction. In other words, the resonator 25 is preferably disposed not to overlap the solar battery 80 in a plan view from the +Z axis direction.

Figure 9:
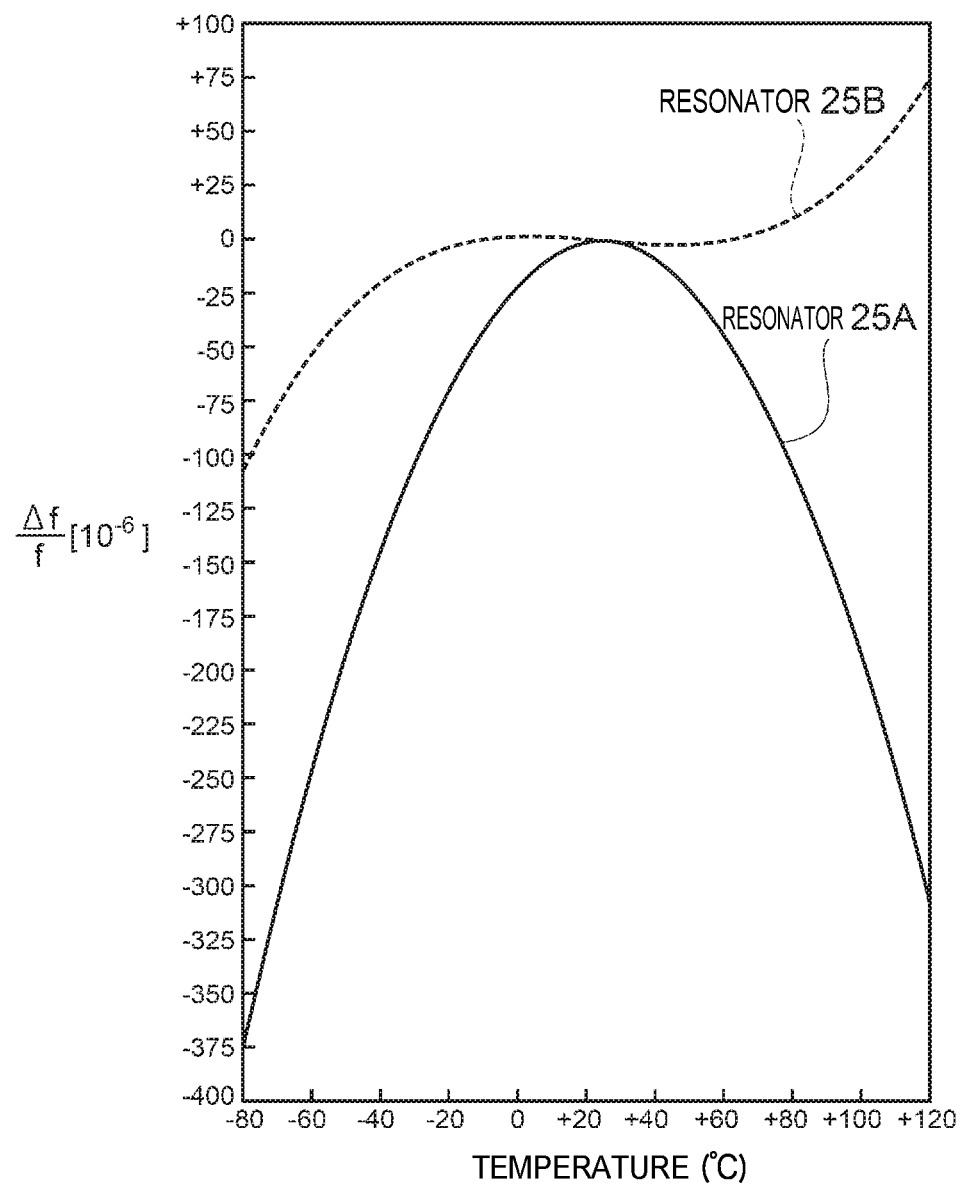
FIG. 9 is a graph illustrating an example of a frequency-temperature characteristic of a resonator.

The resonance element forming the resonator 25 has a so-called frequency-temperature characteristic (hereinafter, referred to as a temperature characteristic) in which a resonance frequency changes depending on a temperature as illustrated in FIG. 9. FIG. 9 is a graph illustrating an example of a frequency-temperature characteristic of the resonator. Particularly, a tuning folk type resonance element, indicated by a resonator 25A in FIG. 9, which generates a reference clock for a clock function and has a resonance frequency of, for example, 32.768 KHz, has a temperature characteristic along a quadratic curve which has a peak substantially near 25° C., and is thus an electronic component in which a frequency change easily occurs with respect to the temperature of an installation environment.

As the resonator 25 outputting a timing reference signal for data processes, for example, an AT cut resonance element, indicated by a resonator 25B in FIG. 9, which has a temperature characteristic along a cubic curve and an output frequency of several MHz to several tens of MHz is used. The AT cut resonance element having the temperature characteristic of the cubic curve has a smaller frequency change around the ordinary temperature than that of the tuning fork type element having the temperature characteristic of the quadratic curve, but has an increasing frequency change with respect to a temperature change in a low temperature region or a high temperature region.

As mentioned above, since even the resonator 25 of which a resonance frequency changes with respect to a temperature change is located such that the solar battery 80 is disposed outside the outer edge of the resonator 25 in a plan view from the +Z axis direction as described above, even if areas of the light reception surfaces 80a, 80b, 80c, and 80d of the solar battery 80 are increased, radiant heat of the solar battery 80 of which the temperature increases due to energy of light is hardly transmitted to the resonator 25, and thus it is possible to suppress the influence on the accuracy (a change in an oscillation frequency according to a temperature characteristic) of an oscillation frequency of the resonator 25, so that it is possible to increase a power generation amount of the solar battery 80.

The GPS antenna 28 is included in the GPS reception unit 160 along with a signal processing portion 66, and receives a plurality of satellite signals. The signal processing portion 66 performs positioning calculation on the basis of the plurality of satellite signals received by the GPS antenna 28, and acquires position information of the user.

The communication unit 29 transmits the pulse wave information or the body motion information, or the position information of the user transmitted from the CPU 21 to the portable apparatus 300 or the like as necessary.

The optical sensor unit 40 as a biological information measurement unit measures a pulse wave or the like, and includes the light receiving portion 41, and a plurality of (in the present embodiment, two) light emitting portions 42 disposed on both sides of the light receiving portion 41, that is, outside the light receiving portion 41 (on the outer circumferential side of the case 31) in a plan view. As mentioned above, since the light receiving portion 41 is disposed inside the light emitting portion 42, it is possible to prevent external light entered from the outer circumferential side of the case 31 from entering the light receiving portion 41, and thus to reduce the influence of the external light on the optical sensor unit 40. The number of light emitting portions 42 is not limited to two, and may be one or three or more. The light receiving portion 41 and the two light emitting portions 42 are attached to one surface of a sensor substrate 43, and are covered with a transparent cover 44 which is formed of a light-transmissive member made of a thermosetting resin. A portion of the transparent cover 44 including a region corresponding to the light receiving portion 41 and the two light emitting portions 42 is inserted into the measurement window portion 45 provided in the case 31. The transparent cover 44 may protrude from the top of the protrusion portion 32 of the case 31.

As described above, in the optical sensor unit 40, a subject (measurement target object) is irradiated with light emitted from the light emitting portion 42, and reflected light is received by the light receiving portion 41, and thus pulse wave information is measured. The optical sensor unit 40 outputs a signal detected by the pulse wave sensor including the light emitting portion 42 and the light receiving portion 41, as a pulse wave measurement signal. For example, a photoelectric sensor is used as the optical sensor unit 40. In this case, there may be a method in which reflected light or transmitted light of light applied to a living body (the wrist of the user) from the light emitting portion 42 is detected by the light receiving portion 41. In this method, since an amount of applied light absorbed or reflected in the living body differs depending on a blood flow rate in a blood vessel, sensor information detected by the photoelectric sensor is converted into a signal corresponding to the blood flow rate, and information regarding pulsation can be acquired by analyzing the signal. However, a pulse wave sensor is not limited to a photoelectric sensor, and may employ other sensors such as an electrocardiograph or an ultrasonic sensor.

As illustrated in FIG. 5A, the optical sensor unit 40 is disposed at a position not overlapping the annularly formed solar battery 80 in a plan view from the direction (+Z axis direction) facing the light reception surfaces 80a, 80b, 80c, and 80d of the solar battery 80. In other words, in a plan view from the +Z axis direction, the solar battery 80 is disposed outside the outer edge of the optical sensor unit 40, and is disposed at the position where the solar battery 80 and the optical sensor unit 40 do not overlap each other. That is, the solar battery 80 is disposed between the bezel 57 and the optical sensor unit 40 in a plan view from the +Z axis direction. Here, the outer edge of the optical sensor unit 40 is preferably an outer edge of a region, obliquely hatched in FIG. 5A, which includes outer edges of at least the light receiving portion 41 and the two light emitting portions 42, and connects the outer edges thereof to each other. In the present embodiment, the outer edge of the optical sensor unit 40 may be an outer edge of the measurement window portion 45 including the light receiving portion 41 and the two light emitting portions 42. The outer edge of the optical sensor unit 40 may be an outer edge of the sensor substrate 43. The outer edge of the optical sensor unit 40 may be the outer edge of the transparent cover 44. A case where the optical sensor unit 40 is surrounded by the solar battery 80 may include a case where the optical sensor unit 40 is surrounded by a plurality of solar batteries 80, and the solar battery 80 may be divided into a plurality of parts or may have cutouts. Here, the term "being surrounded" may be defined in a case where, when a perpendicular is drawn to the outer edge of the optical sensor unit 40, a proportion of the optical sensor unit to which a perpendicular intersecting the solar battery 80 is drawn is 50% or more in a plan view from the +Z axis direction. In addition, the term "being surrounded" may be defined in a case where, when a concentric circle is drawn with respect to the center of the optical sensor unit 40, a proportion at which the concentric circle and the solar battery 80 overlap each other with respect to a circumference of the concentric circle is 50% or more in a plan view from the +Z axis direction.

As mentioned above, since the solar battery 80 annularly disposed is located outside the outer edge of the optical sensor unit 40 so as to surround the optical sensor unit 40 in a plan view from the +Z axis direction, that is, the optical sensor unit 40 is disposed at the center of the case 31 in a plan view, and thus the influence of the external light (stray light) on the optical sensor unit 40 can be reduced. Consequently, the solar battery 80 can be disposed without lowering measurement accuracy in the optical sensor unit 40. Since the solar battery 80 is disposed outside the outer edge of the optical sensor unit 40 in a plan view, a disposition balance for facilitating detection in the optical sensor unit 40 is improved, while efficiently performing power generation in the solar battery 80, and thus it is possible to improve mountability of the apparatus main body 30 of the wrist apparatus 200 for a user. The outer edge of the optical sensor unit 40 may be the outer edge of the transparent cover 44. The term "not overlapping" indicates a state in which S=0 is satisfied if an area where the solar battery 80 and the optical sensor unit 40 overlap each other in a plan view from the +Z axis direction is indicated by S. A case where the optical sensor unit 40 is surrounded by the solar battery 80 may include a case where the optical sensor unit 40 is surrounded by a plurality of solar batteries 80, and the solar battery 80 may be divided into a plurality of parts or may have cutouts. Here, the term "being surrounded" may include a case where, when a line segment is drawn from one point on a certain outer edge of the solar battery 80 to one point of another outer edge, the line segment overlaps the solar battery 80 in a plan view from the +Z axis direction.

As illustrated in FIG. 5A, at least a part of the optical sensor unit 40 is preferably disposed to overlap the centroid G of the solar battery 80 in a plan view from the +Z axis direction. With this disposition of the optical sensor unit 40 and the solar battery 80, a balance (centroid position) of the apparatus main body 30 is favorable, and thus mountability for a user can be improved. The centroid G may be replaced with the center of mass. In a case of a solid object, the centroid G may be defined in a structure of the solid object, or may be defined in a space. The term "overlapping the centroid" may be defined as a state of overlapping the centroid in a case where the position of the centroid is projected onto a two-dimensional plane or a predetermined target object when viewed from a predetermined direction.

The display unit 50 is configured to allow the user to visually recognize numbers, icons, or time display indicators displayed on a display member such as the display panel 60 provided directly under the windshield plate 55, through the windshield plate 55. In other words, in the present embodiment, various pieces of information such as measured biological information or information indicating a workout state are displayed by using the display panel 60, and the display is presented to the user from the front side (in the +Z axis direction). As the display member, instead of the display panel 60 which is a liquid crystal display, an organic electroluminescence (EL) display, an electrophoretic display (EPD), or a light emitting diode (LED) display may be used.

The illumination unit 61 functions as a backlight of the display panel 60. The illumination unit 61 is connected to the front surface 20f as a first surface of the circuit board 20. Since the illumination unit 61 is connected to the circuit board 20 as described above, routing of a wiring for connection can be made the minimum, and it is also possible to block light emitted from the illumination unit 61 with the circuit board 20, and thus to reduce the influence of stray light on the optical sensor unit 40.

The secondary battery 70 has both of polarity terminals connected to the circuit board 20 via a connection board (not illustrated), and supplies power to a circuit controlling a power source. The secondary battery 70 is electrically connected to the solar battery 80 via the circuit board 20. The power is converted into predetermined voltages by the circuit, so as to be supplied to respective circuits, and thus to drive a circuit which drives the optical sensor unit 40 to measure a pulse, a circuit which drives the display panel 60, and a control circuit (CPU 21) which controls the respective circuits. The secondary battery 70 is charged via a pair of charging terminals which are electrically connected to the circuit board 20 via a conduction member (not illustrated) such as a coil spring, or is charged by using power generated by the solar battery 80.

The secondary battery 70 is preferably disposed at a position not overlapping the solar battery 80 in a plan view from the +Z axis direction. As mentioned above, since the secondary battery 70 is preferably disposed at the position not overlapping the solar battery 80 in a plan view from the +Z axis direction, the solar battery 80 is hardly influenced by heat generation during charging of the secondary battery 70, and therefore it is possible to suppress a temperature increase in the solar battery 80 and thus to increase power generation efficiency in the solar battery 80.

The solar battery (solar cell) 80 generates power by converting light energy of external light such as sunlight into power by using a photoelectromotive force effect. The solar battery 80 of the present embodiment is disposed to be divided into four panels between the windshield plate 55 and the display panel 60, and the light reception surfaces $80a$, $80b$, $80c$, and $80d$ of the respective panels are disposed to be directed in the +Z axis direction. The solar battery 80 is disposed on an outer circumferential portion (the outer edge of the display unit 50) including the outer edge of the display panel 60, that is, disposed on the outer circumferential side of the case 31, and is formed in a so-called annular shape (ring shape) of which the central portion has a penetration hole.

Specifically, as illustrated in FIG. 5A, the solar battery 80 has an outer circumference $80os$ which is located on the opening $31s$ of the case 31 and has a circumferential shape along the opening $31s$, a circumferential inner circumference $80is$ of which a circumferential length is shorter than that of the outer circumference $80os$, and two lateral sides $80ss$ connecting the outer circumference $80os$ to the inner circumference $80is$ on both sides, and is disposed at an outer circumferential portion of the display panel 60. In other words, the respective panels having the light reception surfaces $80a$, $80b$, $80c$, and $80d$ have inner circumferences of which circumferential lengths are shorter than those of the outer circumferences. In other words, in a plan view from the +Z axis direction, among concentric circles of the solar battery 80, a concentric circle with a shorter radius may be an inner circumference, and a concentric circle with a longer radius may be an outer circumference. The solar battery 80 in this configuration is formed by disposing the four panels respectively having the light reception surfaces $80a$, $80b$, $80c$, and $80d$ along the opening $31s$ of the case 31. Respective lengths obtained by adding the outer circumferences $80os$ and the inner circumferences $80is$ of the four panels forming the solar battery 80 may be an outer circumferential length and an inner circumferential length of the solar battery 80. With the disposition of the annular solar battery 80, a display region of the display unit 50 can be efficiently disposed, and thus it is possible to increase designability of the wrist apparatus 200.

In this configuration, the annular solar battery 80 using the four panels is exemplified, but the solar battery 80 may be formed of an integrated panel. In a case where the solar battery 80 is formed of a plurality of panels, any number of panels may be used. Any shapes of panels forming the solar battery 80 may be used. The solar battery 80 may be formed of a film instead of a panel.

Any shape of the panel forming the solar battery 80 may be used unless the shape impairs the visibility or designability of the display unit 50. Hereinafter, examples of shapes of the panel will be described in modification examples illustrated in FIGS. 5B and 5C. Here, FIG. 5B is a plan view illustrating Modification Example 1 of a panel of the solar battery, and FIG. 5C is a plan view illustrating Modification Example 2 of a panel of the solar battery.

Figure 5B:
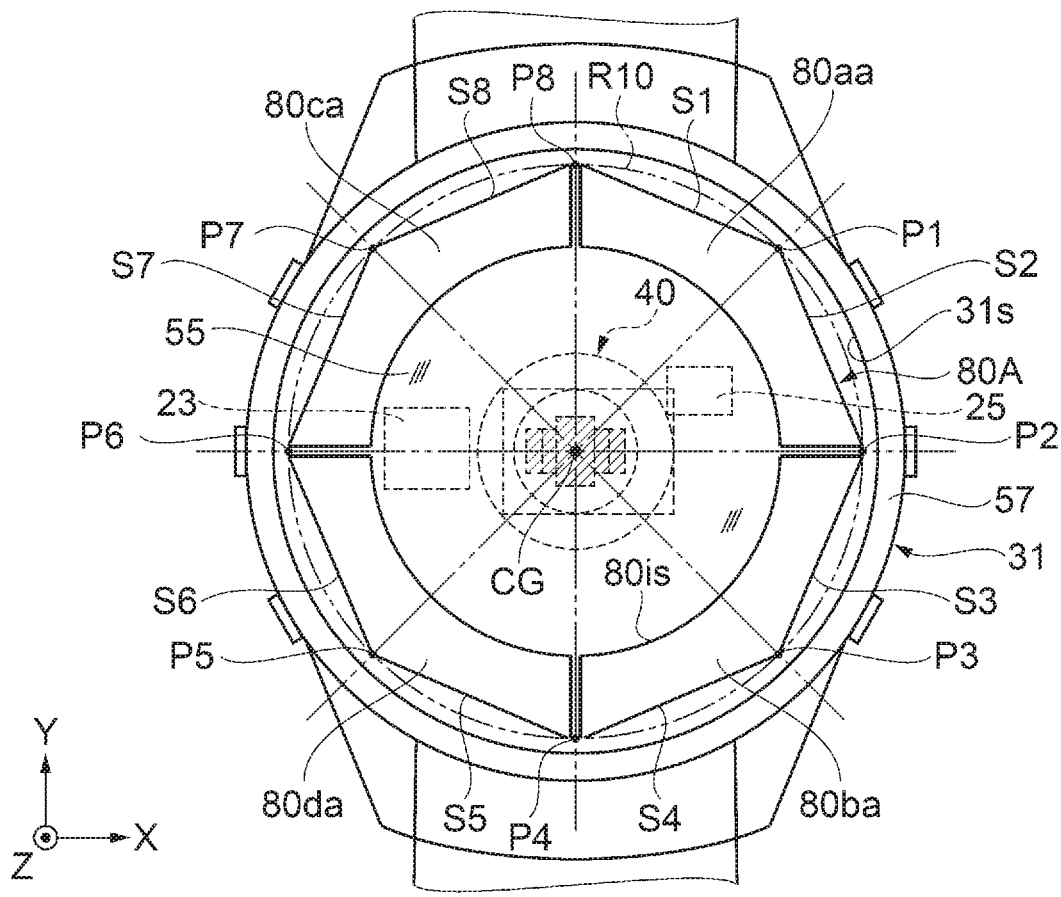
FIG. 5B is a plan view illustrating Modification Example 1 of a panel of a solar battery.

A solar battery 80A according to Modification Example 1 illustrated in FIG. 5B is formed such that an outer circumference of each of panels respectively having light reception surfaces $80aa$, $80ba$, $80ca$, and $80da$ is equally divided into two parts, and thus the outer circumferences are equally divided into eight linear outer circumferential sides s1, s2, s3, s4, s5, s6, s7, and s8 as a whole of the solar battery 80A. Specifically, with the centroid CG of the opening $31s$ as the center, straight lines connecting points P1, P2, P3, P4, P5, P6, P7, and P8 obtained by equally dividing a virtual line R10 which is a concentric circle with the inner edge of the opening $31s$ into eight parts respectively form the outer circumferential sides s1, s2, s3, s4, s5, s6, s7, and s8. For example, in the panel having the light reception surface $80aa$, the outer circumferential side s1 is formed of the straight line connecting the point p8 disposed in the twelve o'clock direction to the point p1 which is the first division point, and the outer circumferential side s2 is formed of the straight line connecting the point p1 to the next division point p2. The inner circumference thereof is formed of a circumference which is a substantially concentric circle with the centroid CG as the center.

Figure 5C:
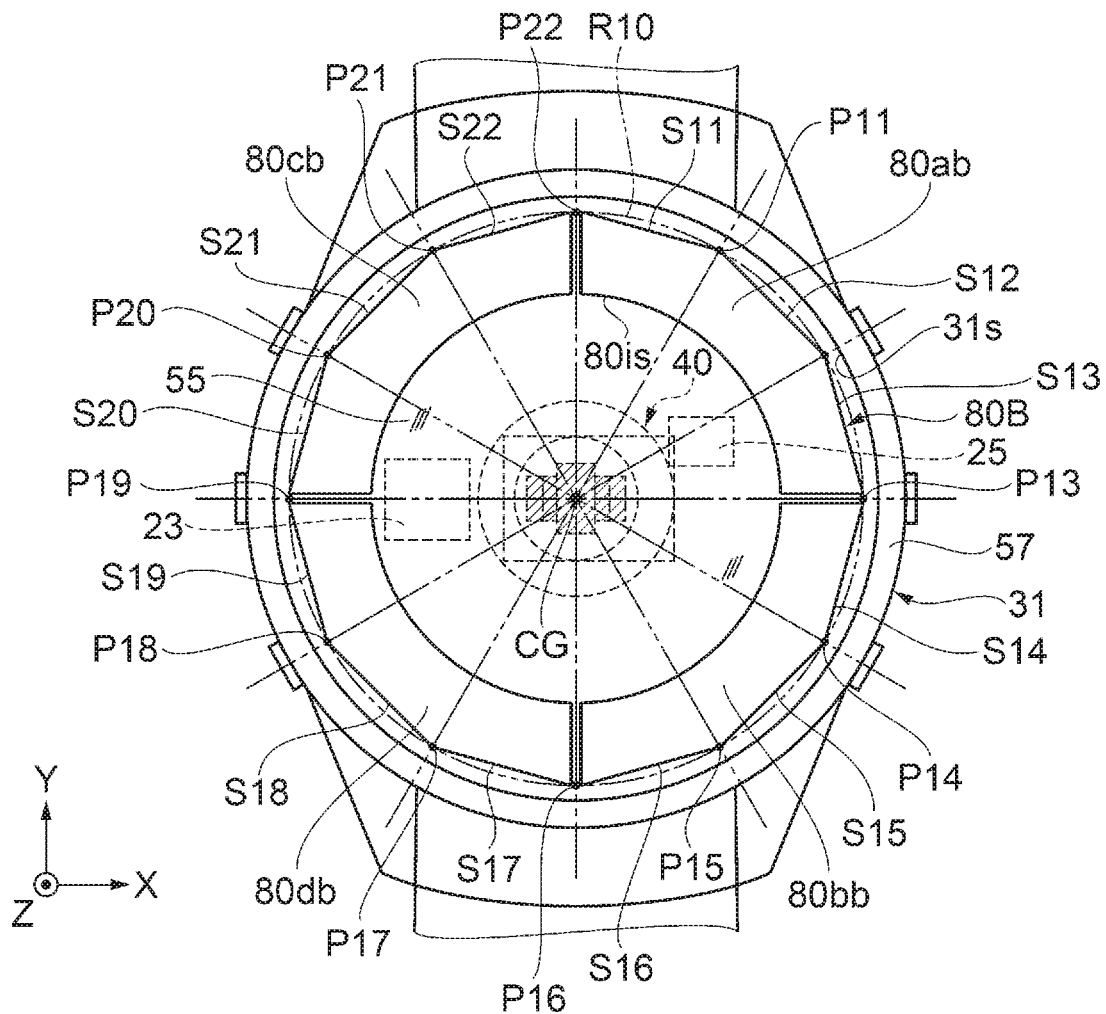
FIG. 5C is a plan view illustrating Modification Example 2 of a panel of a solar battery.

A solar battery 80B according to Modification Example 2 illustrated in FIG. 5C is formed such that an outer circumference of each of panels respectively having light reception surfaces $80ab$, $80bb$, $80cb$, and $80db$ is equally divided into three parts, and thus the outer circumferences are equally divided into twelve linear outer circumferential sides s1, s12, s13, s14, s15, s16, s17, s18, s19, s20, s21, and s22 as a whole of the solar battery 80B. Specifically, with the centroid CG of the opening 31s as the center, straight lines connecting points P11, P12, P13, P14, P15, P16, P17, P18, P19, P20, P21, and P22 obtained by equally dividing a virtual line R10 which is a concentric circle with the inner edge of the opening 31s into twelve parts respectively form the outer circumferential sides s11, s12, s13, s14, s15, s16, s17, s18, s19, s20, s21, and s22. For example, in the panel having the light reception surface 80ab, the outer circumferential side s11 is formed of the straight line connecting the point p22 disposed in the twelve o'clock direction to the point p11 which is the first division point, and the outer circumferential side s12 is formed of the straight line connecting the point p11 to the next division point p12. The inner circumference thereof is formed of a circumference which is a substantially concentric circle with the centroid CG as the center.

In the modification examples as illustrated in FIGS. 5B and 5C, a description has been made of an example in which the inner circumference of the panel is a circumference, and the outer circumference of the panel is equally divided into two parts or three parts, but the inner circumference of the panel may be equally divided into two parts or three parts. The inner circumference and the outer circumference may be equally divided into two parts or three parts. A combination of a panel having a linear inner circumference or outer circumference may be used.

A storage unit 180 stores biological information such as a pulse wave from the optical sensor unit 40, position information from the GPS reception unit 160, and body motion information from the body motion sensor unit 170, under the control of the CPU 21.

According to the wrist apparatus 200 as a portable electronic apparatus, in a plan view from the +Z axis direction, the solar battery 80 has the outer circumference 80os along the opening 31s of the case 31 and the inner circumference 80is of which a circumferential length is shorter than the outer circumference 80os, and is disposed at the outer circumferential portion of the display panel 60 outside the outer edge of the acceleration sensor 23. Since the acceleration sensor 23 is disposed at the position not overlapping the solar battery 80 inside the solar battery 80, the acceleration sensor 23 can be efficiently disposed in a space of the apparatus main body 30 in the thickness direction thereof, and thus the apparatus main body 30 can be thinned compared with a case where the solar battery 80 and the acceleration sensor 23 are disposed to overlap each other.

Since the solar battery 80 is disposed outside the outer edge of the resonator 25 in a plan view from the +Z axis direction, even if areas of the light reception surfaces 80a, 80b, 80c, and 80d of the solar battery 80 are increased, radiant heat of the solar battery 80 of which the temperature increases due to energy of light is hardly transmitted to the resonator 25, and thus it is also possible to suppress the influence on the accuracy (a change in an oscillation frequency according to a temperature characteristic) of an oscillation frequency of the resonator 25 of which a resonance frequency changes depending on a temperature change.

According to the wrist apparatus 200, with the disposition of the annular solar battery 80, a display region of the display unit 50 can be efficiently disposed without losing a disposition balance, and thus it is possible to increase designability of the wrist apparatus 200 while increasing a power generation amount of the solar battery 80.

The secondary battery 70 may be disposed between the solar battery 80 and the circuit board 20 in a sectional view from the −Y axis direction which is orthogonal to a plan view from the +Z axis direction. With this disposition, even if areas of the light reception surfaces 80a, 80b, 80c, and 80d of the solar battery 80 are increased, radiant heat of the solar battery 80 of which the temperature increases due to energy of light can be blocked by the secondary battery 70, and thus it is possible to reduce the influence of heat on detection in the acceleration sensor 23 connected to the circuit board 20 or an output frequency of the resonator 25.

Figure 10:
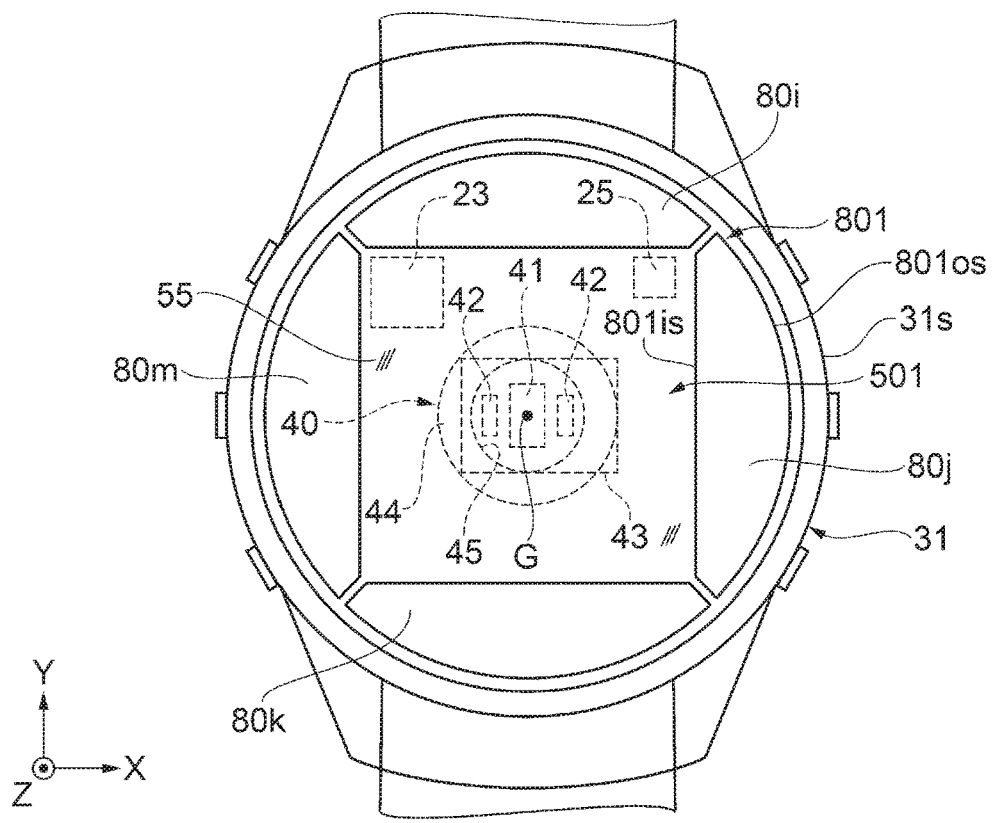
FIG. 10 is a plan view illustrating Modification Example 1 of disposition of the solar battery, an acceleration sensor, and the resonator.
Figure 11:
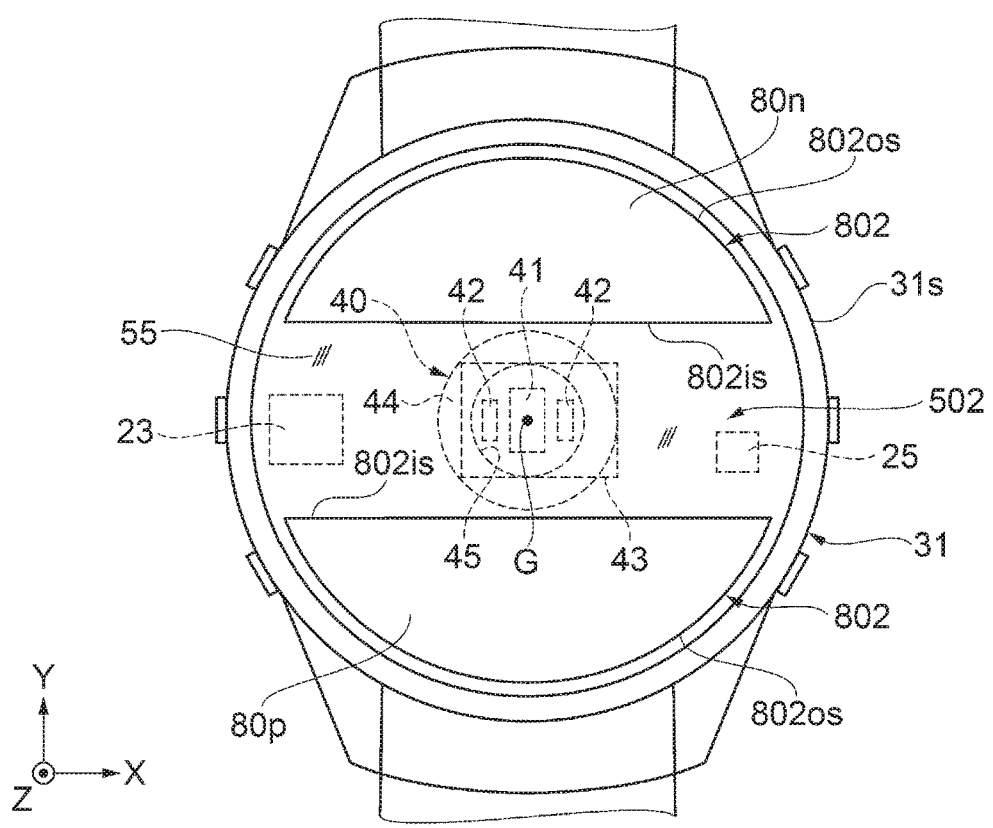
FIG. 11 is a plan view illustrating Modification Example 2 of disposition of the solar battery, the acceleration sensor, and the resonator.
Figure 12:
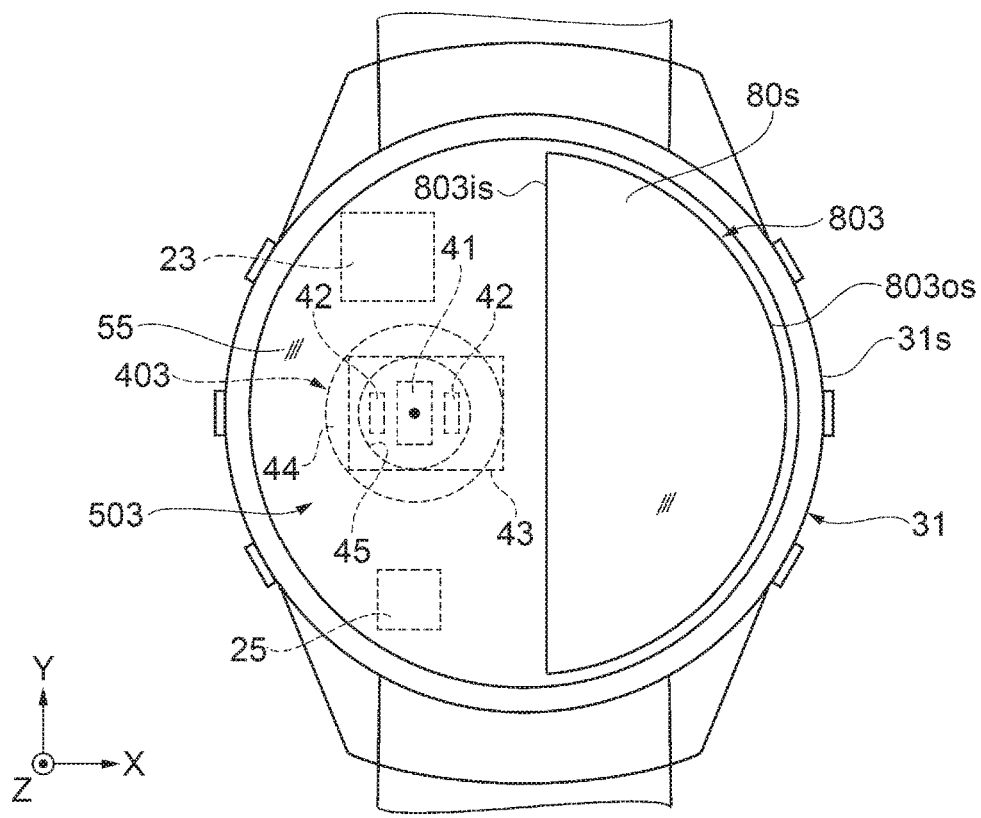
FIG. 12 is a plan view illustrating Modification Example 3 of disposition of the solar battery, the acceleration sensor, and the resonator.
Figure 13:
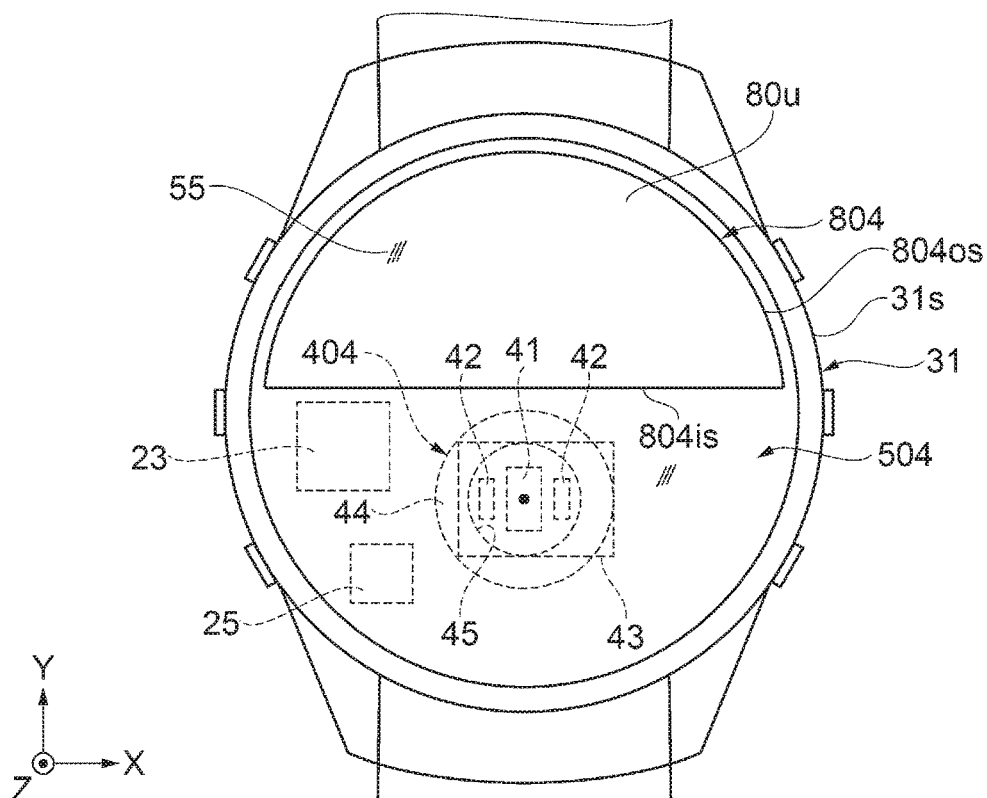
FIG. 13 is a plan view illustrating Modification Example 4 of disposition of the solar battery, the acceleration sensor, and the resonator.

3.1 Modification Example of Disposition of Solar Battery, Acceleration Sensor, and Resonator In the above description, a description has been made of the configuration in which the annular solar battery 80 is disposed on the outer edge side of the display panel 60, and the solar battery 80, the acceleration sensor 23, and the resonator 25 are disposed at positions not overlapping each other in a plan view from the +Z axis direction, but a disposition configuration of the solar battery 80, the acceleration sensor 23, and the resonator 25 is not limited thereto. A disposition and a configuration (shape) of the solar battery 80 and dispositions of the acceleration sensor 23 and the resonator 25 may be realized as described in the following modification examples, for example. A disposition configuration of the solar battery 80, the acceleration sensor 23, and the resonator 25 is not limited to the modification examples, and may employ other configurations. Hereinafter, with reference to FIGS. 10 to 13, Modification Example 1 to Modification Example 4 of disposition of the solar battery, the acceleration sensor 23, and the resonator 25 will be described in this order. FIGS. 10 to 13 are plan views illustrating modification examples of disposition of the solar battery and optical sensor, in which FIG. 10 illustrates Modification Example 1, FIG. 11 illustrates Modification Example 2, FIG. 12 illustrates Modification Example 3, and FIG. 13 illustrates Modification Example 4.

MODIFICATION EXAMPLE 1

With reference to FIG. 10, a description will be made of Modification Example 1 of disposition of the solar battery, the acceleration sensor, and the resonator. As illustrated in FIG. 10, a solar battery 801 according to Modification Example 1 is located (refer to FIG. 4) between the windshield plate 55 and the display panel 60, and is disposed to be divided into four panels at positions having substantially 45 degrees with respect to the X axis and the Y axis, and light reception surfaces 80i, 80j, 80k, and 80m of the respective panels are disposed to be directed in the +Z axis direction. The solar battery 801 has an outer circumference 801os along the opening 31s of the case 31 and an inner circumference 801is of which a circumferential length is shorter than the outer circumference 801os, and is disposed at the outer circumferential portion of the display panel 60. In other words, each of respective panels having the light reception surfaces 80i, 80j, 80k, and 80m has an inner circumference of which a circumferential length is smaller than that of an outer circumference. The solar battery 801 is formed such that the central portion thereof has a rectangular (in this example, a substantially square) penetration hole due to the respective panels having the light reception surfaces 80i, 80j, 80k, and 80m. In other words, in the solar battery 801, an outer circumferential side of each panel has a circular arc shape, a center side thereof has a linear shape, and thus a rectangular display unit 501 is formed. In this configuration, the solar battery 801 using four panels is exemplified, but the solar battery 801 may be formed of an integrated panel not divided.

Here, the acceleration sensor 23 and the resonator 25 are disposed such that the inner circumference 801*is* of the solar battery 801 is located outside the outer edge of the acceleration sensor 23 and outside the outer edge of the resonator 25 in a plan view from the +Z axis direction. In other words, the acceleration sensor 23 and the resonator 25 are disposed at positions not overlapping the solar battery 801 in a plan view from the +Z axis direction, and are mounted on a circuit board (not illustrated). Specifically, the acceleration sensor 23 is disposed inside the inner circumference 801*is* of the solar battery 801 at a portion where the panels having the light reception surface 80*m* and the light reception surface 80*i* are disposed side by side among the panels forming the solar battery 801. The resonator 25 is disposed inside the inner circumference 801*is* of the solar battery 801 at a portion where the panels having the light reception surface 80*i* and the light reception surface 80*j* are disposed side by side.

Here, the optical sensor unit 40 includes at least the sensor substrate 43 connected to the light emitting portions 42 and the light receiving portion 41, and is located at the center of the rectangular (in this example, a substantially square) penetration hole of the solar battery 801 in a plan view from the +Z axis direction. In other words, the optical sensor unit 40 is located inside the solar battery 801 so as not to overlap the solar battery 801, and is disposed to be surrounded by the solar battery 801 in a plan view from the +Z axis direction. The optical sensor unit 40 is disposed to overlap the centroid G of the solar battery 801 in a plan view from the +Z axis direction. A configuration of the optical sensor unit 40 is the same as described above, and thus a description thereof will be omitted here.

According to the disposition of Modification Example 1, the inner circumference 801*is* of the solar battery 801 is disposed outside the outer edges of the acceleration sensor 23 and the resonator 25 in a plan view from the +Z axis direction. In other words, the acceleration sensor 23 and the solar battery 801 are disposed at positions not overlapping each other, and thus the apparatus main body 30 can be thinned more than in a case where the acceleration sensor 23 and the solar battery 801 overlap each other. Since the resonator 25 and the solar battery 801 are disposed at positions not overlapping each other, it is possible to suppress the influence of radiant heat of the solar battery 801 of which the temperature increases due to energy of light on the accuracy (a change in an oscillation frequency according to a temperature characteristic) of an oscillation frequency of the resonator 25. The solar battery 801 can be disposed in the case 31 with good balance.

MODIFICATION EXAMPLE 2

With reference to FIG. 11, a description will be made of Modification Example 2 of disposition of the solar battery, the acceleration sensor, and the resonator. As illustrated in FIG. 11, a solar battery 802 according to Modification Example 2 is formed of two panels in each of which an outer circumferential side forms a circular arc-shaped outer edge and a center side forms a substantially linear outer edge between the windshield plate 55 and the display panel 60 (refer to FIG. 4), and the substantially linear outer edges are disposed to oppose each other along the X axis and thus to form a display unit 502 between the two panels. Specifically, the solar battery 802 has an outer circumference 802*os* along the opening 31*s* of the case 31 and an inner circumference 802*is* of which a circumferential length is shorter than the outer circumference 802*os*, and is disposed at the outer circumferential portion of the display panel 60. In other words, each of respective panels having light reception surfaces 80*n* and 80*p* has an inner circumference of which a circumferential length is smaller than that of an outer circumference. The light reception surfaces 80*n* and 80*p* of the respective panels forming the solar battery 802 are disposed to be directed in the +Z axis direction.

Here, the acceleration sensor 23 and the resonator 25 are disposed such that the inner circumference 802*is* of the solar battery 802 is located outside the outer edge of the acceleration sensor 23 and outside the outer edge of the resonator 25 in a plan view from the +Z axis direction. In other words, the acceleration sensor 23 and the resonator 25 are disposed at positions not overlapping the solar battery 802 in a plan view from the +Z axis direction, and are mounted on a circuit board (not illustrated). Specifically, the acceleration sensor 23 is disposed on the outer circumferential side of the case 31 in the −X axis direction on the X axis passing through the centroid G of the solar battery 802 between the light reception surface 80*n* and the light reception surface 80*p* of the two panels forming the solar battery 802. The resonator 25 is disposed on the outer circumferential side of the case 31 in the +X axis direction on the X axis passing through the centroid G of the solar battery 802 between the light reception surface 80*n* and the light reception surface 80*p* of the two panels forming the solar battery 802.

Here, the optical sensor unit 40 includes at least the sensor substrate 43 connected to the light emitting portions 42 and the light receiving portion 41, and is located at the center of the display unit 502 disposed between two solar batteries 802 in a plan view from the +Z axis direction. In other words, the optical sensor unit 40 is disposed at a position not overlapping the solar battery 802 in a plan view from the +Z axis direction. The optical sensor unit 40 is disposed to overlap the centroid G of the solar battery 802 in a plan view from the +Z axis direction. A configuration of the optical sensor unit 40 is the same as described above, and thus a description thereof will be omitted here.

Here, according to the disposition of Modification Example 2, the inner circumference 802*is* of the solar battery 802 is located outside the outer edge of the acceleration sensor 23 and outside the outer edge of the resonator 25 in a plan view from the +Z axis direction. In other words, the acceleration sensor 23 and the solar battery 802 are disposed at positions not overlapping each other, and thus the apparatus main body 30 can be thinned more than in a case where the acceleration sensor 23 and the solar battery 802 overlap each other. Since the resonator 25 and the solar battery 802 are disposed at positions not overlapping each other, it is possible to suppress the influence on the accuracy (a change in an oscillation frequency according to a temperature characteristic) of an oscillation frequency of the resonator 25. The solar battery 802 can be disposed in the case 31 with good balance.

MODIFICATION EXAMPLE 3

With reference to FIG. 12, a description will be made of Modification Example 3 of disposition of the solar battery, the acceleration sensor, and the resonator. A solar battery 803 according to Modification Example 3 illustrated in FIG. 12 is located on the outer edge side of the display panel 60 between the windshield plate 55 and the display panel 60 (refer to FIG. 4), and is formed of a semicircular single panel of which an outer circumferential side forms a circular arc-shaped outer edge and a center side forms a substantially linear outer edge along the Y axis. Specifically, the solar battery 803 has an outer circumference 803os along the opening 31s of the case 31 and an inner circumference 803is of which a circumferential length is shorter than the outer circumference 803os, and is disposed at one outer circumferential portion of the display panel 60. The solar battery 803 is disposed on the +X axis side (three o'clock side) of the case 31. Therefore, a display unit 503 is disposed on the −X axis side (nine o'clock side) of the case 31. A light reception surface 80s of the panel forming the solar battery 803 is disposed to be directed in the +Z axis direction.

Here, the acceleration sensor 23 and the resonator 25 are disposed such that the inner circumference 803is of the solar battery 803 is located outside the outer edge of the acceleration sensor 23 and outside the outer edge of the resonator 25 in a plan view from the +Z axis direction. In other words, the acceleration sensor 23 and the resonator 25 are disposed at positions not overlapping the solar battery 803 in a plan view from the +Z axis direction, and are mounted on a circuit board (not illustrated). Specifically, the acceleration sensor 23 and the resonator 25 are located further toward the −X axis side than the position where the light reception surface 80s of the panel forming the solar battery 803 is disposed, and are disposed at positions overlapping a display unit 503 on the outer circumferential side of the case 31.

An optical sensor unit 403 includes at least the sensor substrate 43 connected to the light emitting portions 42 and the light receiving portion 41, and the measurement window portion 45 thereof is disposed at a position deviated in the −X axis direction from the center of the case 31 so as not to overlap the solar battery 803 in a plan view from the +Z axis direction. In a case where the solar battery 803 is disposed to be biased, the optical sensor unit 403 may be disposed to match the centroid G. A configuration of the optical sensor unit 403 is the same as the configuration of the optical sensor unit 40 except for the disposition position, and thus a description thereof will be omitted here.

Here, according to the disposition of Modification Example 3, the inner circumference 803is of the solar battery 803 is located outside the outer edge of the acceleration sensor 23 and outside the outer edge of the resonator 25 in a plan view from the +Z axis direction. In other words, the acceleration sensor 23 and the solar battery 803 are disposed at positions not overlapping each other, and thus the apparatus main body 30 can be thinned more than in a case where the acceleration sensor 23 and the solar battery 803 overlap each other. Since the resonator 25 and the solar battery 803 are disposed at positions not overlapping each other, it is possible to suppress the influence of radiant heat of the solar battery 803 of which the temperature increases due to energy of light on the accuracy (a change in an oscillation frequency according to a temperature characteristic) of an oscillation frequency of the resonator 25.

According to the disposition of Modification Example 3, the +X axis side (three o'clock side) of the case 31 is often located at the fingertip side of the user when the wrist apparatus 200 is mounted on the user's wrist, and is thus hardly hooked by clothes (sleeve) of the user. Therefore, in a case where the solar battery 803 is disposed on the +X axis side (three o'clock side) of the case 31 as in Modification Example 3, it is possible to increase a probability that sunlight may be received and also to perform more efficient power generation.

MODIFICATION EXAMPLE 4

With reference to FIG. 13, a description will be made of Modification Example 4 of disposition of the solar battery, the acceleration sensor, and the resonator. A solar battery 804 according to Modification Example 4 illustrated in FIG. 13 is located on the outer edge side of the display panel 60 between the windshield plate 55 and the display panel 60 (refer to FIG. 4), and is formed of a semicircular single panel of which an outer circumferential side forms a circular arc-shaped outer edge (outer circumference) and a center side forms a substantially linear outer edge (inner circumference) along the X axis. Specifically, the solar battery 804 has an outer circumference 804os along the opening 31s of the case 31 and an inner circumference 804is of which a circumferential length is shorter than the outer circumference 804os, and is disposed at one outer circumferential portion of the display panel 60. The solar battery 804 is disposed on the +Y axis side (twelve o'clock side) of the case 31. Therefore, a display unit 504 is disposed on the −Y axis side (six o'clock side) of the case 31. A light reception surface 80u of the panel forming the solar battery 804 is disposed to be directed in the +Z axis direction.

Here, the acceleration sensor 23 and the resonator 25 are disposed such that the inner circumference 804is of the solar battery 804 is located outside the outer edge of the acceleration sensor 23 and outside the outer edge of the resonator 25 in a plan view from the +Z axis direction. In other words, the acceleration sensor 23 and the resonator 25 are disposed at positions not overlapping the solar battery 804 in a plan view from the +Z axis direction, and are mounted on a circuit board (not illustrated). Specifically, the acceleration sensor 23 and the resonator 25 are located further toward the −Y axis side than the position where the light reception surface 80u of the panel forming the solar battery 804 is disposed, and are disposed at positions overlapping a display unit 504 on the outer circumferential side of the case 31.

An optical sensor unit 404 includes at least the sensor substrate 43 connected to the light emitting portions 42 and the light receiving portion 41, and the measurement window portion 45 thereof is disposed at a position deviated in the −Y axis direction from the center of the case 31 so as not to overlap the solar battery 804 in a plan view from the +Z axis direction. A configuration of the optical sensor unit 404 is the same as the configuration of the optical sensor unit 40 except for the disposition position, and thus a description thereof will be omitted here.

Here, according to the disposition of Modification Example 4, the inner circumference 804is of the solar battery 804 is located outside the outer edge of the acceleration sensor 23 and outside the outer edge of the resonator 25 in a plan view from the +Z axis direction. In other words, the acceleration sensor 23 and the solar battery 804 are disposed at positions not overlapping each other, and thus the apparatus main body 30 can be thinned more than in a case where the acceleration sensor 23 and the solar battery 804 overlap each other. Since the resonator 25 and the solar battery 804 are disposed at positions not overlapping each other, it is possible to suppress the influence of radiant heat of the solar battery 804 of which the temperature increases due to energy of light on the accuracy (a change in an oscillation frequency according to a temperature characteristic) of an oscillation frequency of the resonator 25.

In the embodiment, as an example of a positioning system using a position information satellite, a description has been made of the GPS using the GPS satellite 8 as a position information satellite included in a global navigation satellite system (GNSS), but this is only an example. The global navigation satellite system may include other systems such as Galileo (EU), GLONASS (Russia), or BeiDou (China), or a positioning information satellite transmitting a satellite signal, for example, a stationary satellite or a quasi-zenith satellite such as SBAS. In other words, the wrist apparatus 200 may be configured to acquire any one of date information, time information, position information, and speed information obtained by processing electric waves (radio signals) from position information satellites including satellites other than the GPS satellites 8. Instead of the global navigation satellite system, a regional navigation satellite system (RNSS) may be used.

What is claimed is:

1. A portable electronic apparatus comprising:
a case;
a display unit that is provided in the case, and has a display surface;
an annular solar battery that is disposed outside the display surface in a plan view from a normal direction to the display surface;
an acceleration sensor that is provided in the case, and is disposed at a position overlapping the display surface in the plan view;
a circuit board having a first surface and an opposed second surface, wherein the acceleration sensor and an illumination unit are provided on the first surface, and a biological information measurement unit measuring biological information is provided on the second surface not overlapping the annular solar battery in the plan view; and
a secondary battery electrically connected to the solar battery, wherein the secondary battery is disposed at a position overlapping the acceleration sensor and the biological information measurement unit in the plan view, and the illumination unit is disposed at a position not overlapping the annular solar battery and the biological information measurement unit in the plan view.

2. The portable electronic apparatus according to claim 1, further comprising: wherein the solar battery is disposed outside an outer edge of the biological information measurement unit in the plan view.

3. The portable electronic apparatus according to claim 2, wherein, in the sectional view, the circuit board is disposed above the biological information measurement unit, and the solar battery is disposed above the circuit board.

4. The portable electronic apparatus according to claim 1, wherein the biological information measurement unit includes a light emitting portion and a light receiving portion, and
wherein the light emitting portion is disposed outside the light receiving portion in the plan view.

* * * * *